United States Patent
Cho et al.

(10) Patent No.: US 9,963,721 B2
(45) Date of Patent: May 8, 2018

(54) METHOD OF SCREENING GENE FOR 1,4-BDO PRODUCTION

(71) Applicant: Samsung Electronics Co., Ltd., Suwon-si, Gyeonggi-do (KR)

(72) Inventors: Hwayoung Cho, Hwaseong-si (KR); Jinhwan Park, Suwon-si (KR); Yukyung Jung, Hwaseong-si (KR); Jaechan Park, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 38 days.

(21) Appl. No.: 14/913,767

(22) PCT Filed: Aug. 22, 2014

(86) PCT No.: PCT/KR2014/007821
§ 371 (c)(1),
(2) Date: Feb. 23, 2016

(87) PCT Pub. No.: WO2015/026195
PCT Pub. Date: Feb. 26, 2015

(65) Prior Publication Data
US 2016/0208292 A1    Jul. 21, 2016

(30) Foreign Application Priority Data

Aug. 23, 2013  (KR) .................. 10-2013-0100567

(51) Int. Cl.
*C12P 7/18*     (2006.01)
*C12N 1/21*     (2006.01)
*C07K 14/34*    (2006.01)
*C12N 9/10*     (2006.01)
*C12N 9/04*     (2006.01)
*C12Q 1/48*     (2006.01)

(52) U.S. Cl.
CPC .............. *C12P 7/18* (2013.01); *C07K 14/34* (2013.01); *C12N 9/0006* (2013.01); *C12N 9/1025* (2013.01); *C12Q 1/48* (2013.01); *C12Y 203/03001* (2013.01); *C12Y 101/01027* (2013.01); *G01N 2333/91045* (2013.01)

(58) Field of Classification Search
None
See application file for complete search history.

(56) References Cited

U.S. PATENT DOCUMENTS

| 6,962,989 | B1* | 11/2005 | Pompejus ............... C07H 21/02 530/350 |
| 7,858,350 | B2 | 12/2010 | Burk et al. |
| 8,067,214 | B2 | 11/2011 | Burk et al. |
| 8,129,155 | B2 | 3/2012 | Trawick et al. |
| 8,129,156 | B2 | 3/2012 | Burk et al. |
| 8,129,169 | B2 | 3/2012 | Van Dien et al. |
| 8,178,327 | B2 | 5/2012 | Burk et al. |
| 2011/0201068 | A1 | 8/2011 | Pharkya et al. |
| 2013/0217086 | A1 | 8/2013 | Lee et al. |
| 2014/0030781 | A1 | 1/2014 | Lee et al. |

FOREIGN PATENT DOCUMENTS

| KR | 2007-0096348 A | 10/2007 |
| KR | 2011-0117131 A | 10/2011 |
| KR | 2012-0025450 A | 3/2012 |
| WO | WO 2010-141920 A2 | 12/2010 |

OTHER PUBLICATIONS

Zhou et al., Cell Mol Life Sci 63:2260-2290, 2006.*
Kozak, M., Gene 234:187-208, 1999.*
Frunzke et al., J. Bacteriol. 193:1212-1221, 2011.*
Oxford online dictionary definition of "overexpress", obtained from https://en.oxforddictionaries.com/, last viewed on Aug. 1, 2017, 1 page.*
International Search Report in PCT/KR2014/007821 dated Nov. 7, 2014.
NCBI, Reference sequence No. WP_011013797.1 (May 15, 2013).
NCBI, Reference sequence No. NP_601429.1 (Jul. 22, 2013).

* cited by examiner

*Primary Examiner* — David Steadman
(74) *Attorney, Agent, or Firm* — Leydig, Voit & Mayer, Ltd.

(57) ABSTRACT

Provided is a screening method of discovering genes capable of increasing 1,4-BDO production on the basis of proteomics data. Over-expression of proteins screened by the method, NCgl0630 (citrate synthase) and NCgl2145 (hypothetical protein), increase 1,4-BDO productivity. The method may lead to screening of a protein associated with 1,4-BDO productivity, thereby increasing 1,4-BDO productivity, and thus, the method may be recognized as being industrially applicable.

4 Claims, 3 Drawing Sheets

[Fig. 1]
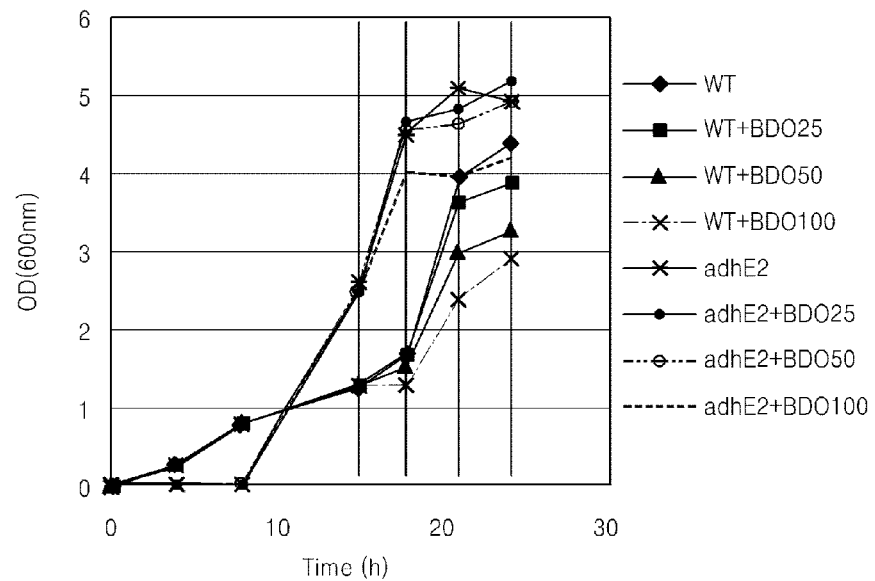
[Fig. 2]
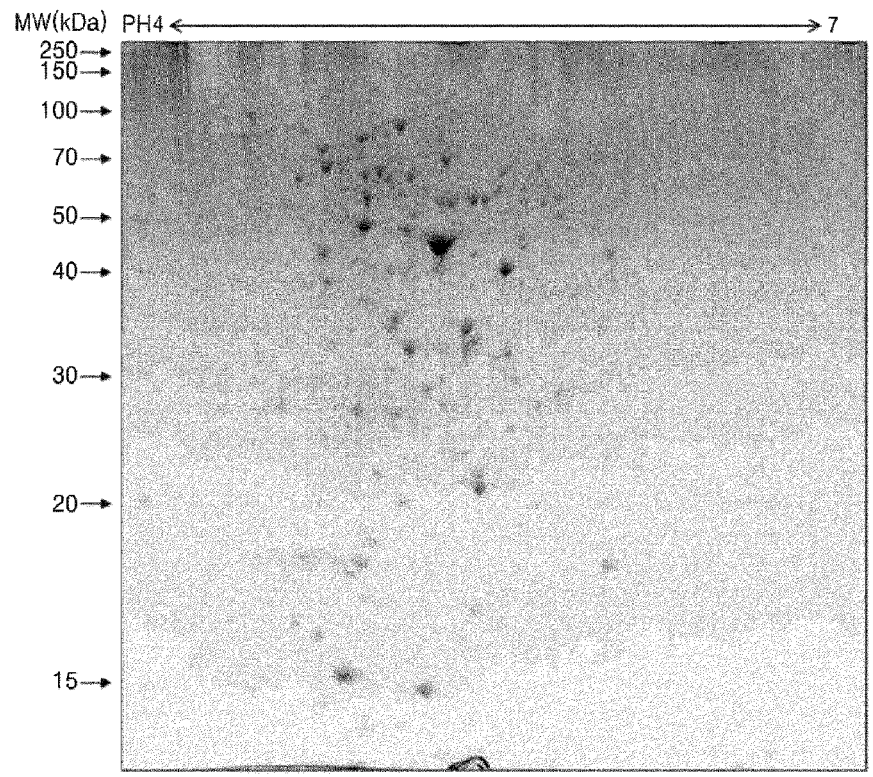

[Fig. 3a]
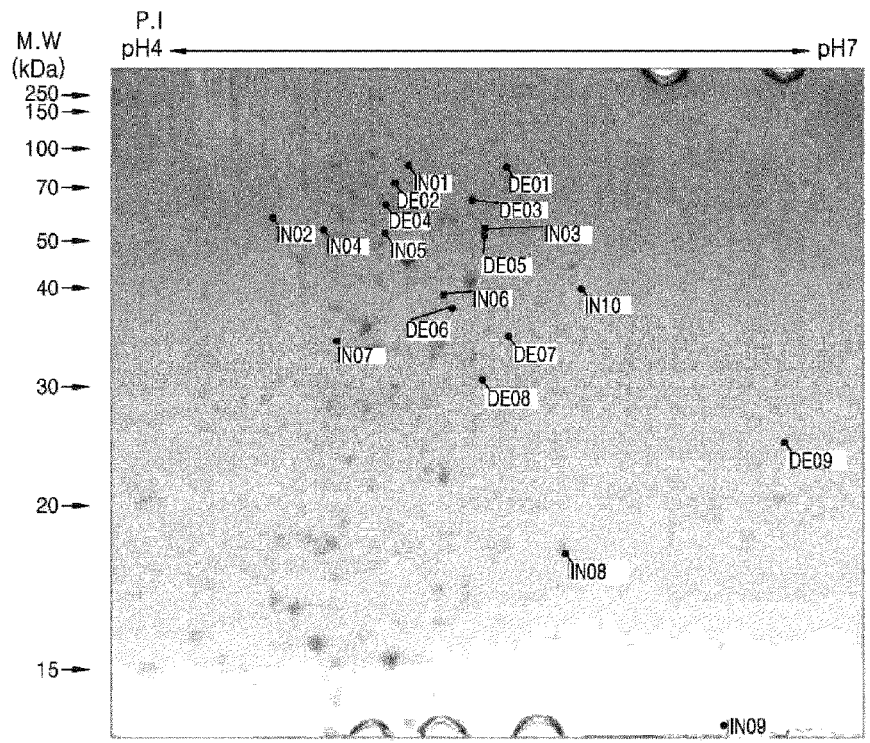
[Fig. 3b]
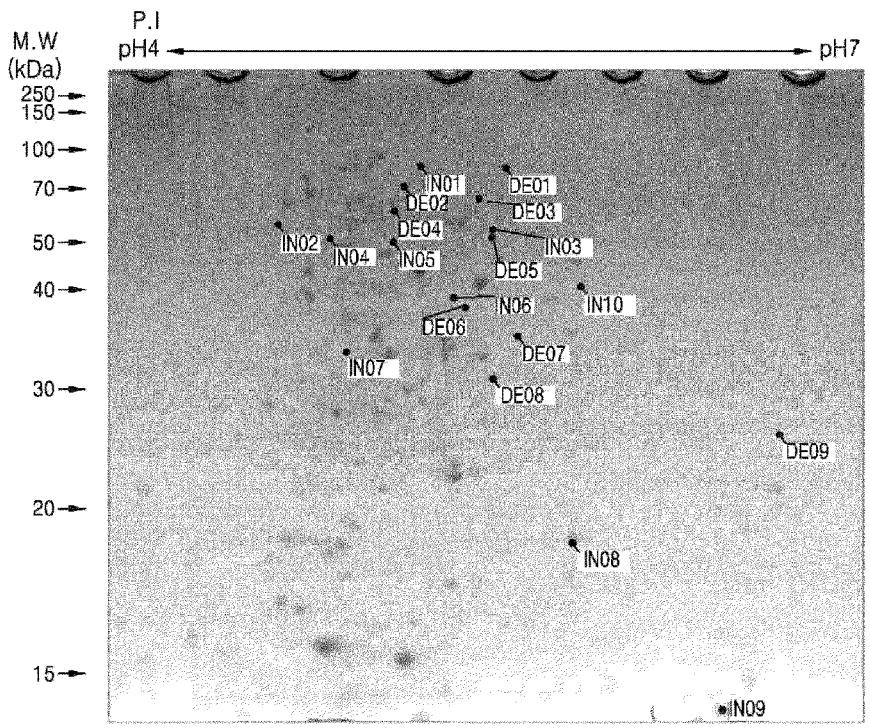

[Fig. 4]
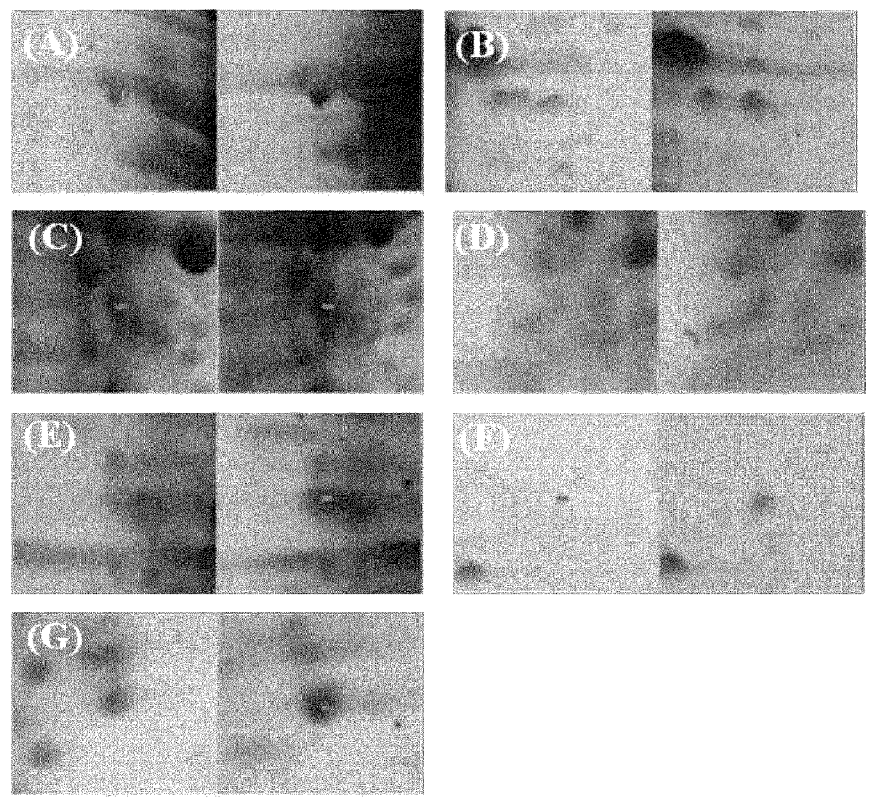
[Fig. 5]
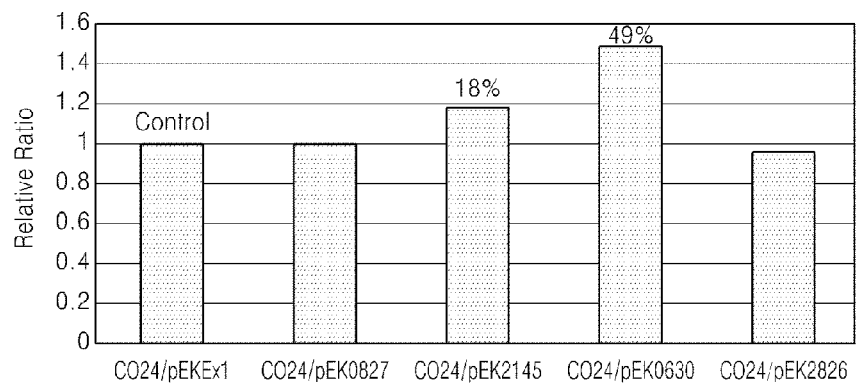

SEQUENCE LISTING

<160> NUMBER OF SEQ ID NOS: 28

<210> SEQ ID NO 1
<211> LENGTH: 383
<212> TYPE: PRT
<213> ORGANISM: Corynebacterium glutamicum

<400> SEQUENCE: 1

```
Met Ser Ser Ala Thr Thr Thr Asp Val Arg Lys Gly Leu Tyr Gly Val
 1               5                  10                  15

Ile Ala Asp Tyr Thr Ala Val Ser Lys Val Met Pro Glu Thr Asn Ser
            20                  25                  30

Leu Thr Tyr Arg Gly Tyr Ala Val Glu Asp Leu Val Glu Asn Cys Ser
        35                  40                  45

Phe Glu Glu Val Phe Tyr Leu Leu Trp His Gly Glu Leu Pro Thr Ala
    50                  55                  60

Gln Gln Leu Ala Glu Phe Asn Glu Arg Gly Arg Ser Tyr Arg Ser Leu
65                  70                  75                  80

Asp Ala Gly Leu Ile Ser Leu Ile His Ser Leu Pro Lys Glu Ala His
                85                  90                  95

Pro Met Asp Val Met Arg Thr Ala Val Ser Tyr Met Gly Thr Lys Asp
            100                 105                 110

Ser Glu Tyr Phe Thr Thr Asp Ser Glu His Ile Arg Lys Val Gly His
        115                 120                 125

Thr Leu Leu Ala Gln Leu Pro Met Val Leu Ala Met Asp Ile Arg Arg
130                 135                 140

Arg Lys Gly Leu Asp Ile Ile Ala Pro Asp Ser Ser Lys Ser Val Ala
145                 150                 155                 160

Glu Asn Leu Leu Ser Met Val Phe Gly Thr Gly Pro Glu Ser Pro Ala
                165                 170                 175

Ser Asn Pro Ala Asp Val Arg Asp Phe Glu Lys Ser Leu Ile Leu Tyr
            180                 185                 190

Ala Glu His Ser Phe Asn Ala Ser Thr Phe Thr Ala Arg Val Ile Thr
        195                 200                 205

Ser Thr Lys Ser Asp Val Tyr Ser Ala Ile Thr Gly Ala Ile Gly Ala
    210                 215                 220

Leu Lys Gly Pro Leu His Gly Gly Ala Asn Glu Phe Val Met His Thr
225                 230                 235                 240

Met Leu Ala Ile Asp Asp Pro Asn Lys Ala Ala Ala Trp Ile Asn Asn
                245                 250                 255
```

```
Ala Leu Asp Asn Lys Asn Val Val Met Gly Phe Gly His Arg Val Tyr
            260                 265                 270

Lys Arg Gly Asp Ser Arg Val Pro Ser Met Glu Lys Ser Phe Arg Glu
            275                 280                 285

Leu Ala Ala Arg His Asp Gly Glu Lys Trp Val Ala Met Tyr Glu Asn
            290                 295                 300

Met Arg Asp Ala Met Asp Ala Arg Thr Gly Ile Lys Pro Asn Leu Asp
305                 310                 315                 320

Phe Pro Ala Gly Pro Ala Tyr His Leu Leu Gly Phe Pro Val Asp Phe
                325                 330                 335

Phe Thr Pro Leu Phe Val Ile Ala Arg Val Ala Gly Trp Thr Ala His
            340                 345                 350

Ile Val Glu Gln Tyr Glu Asn Asn Ser Leu Ile Arg Pro Leu Ser Glu
            355                 360                 365

Tyr Asn Gly Glu Glu Gln Arg Glu Val Ala Pro Ile Glu Lys Arg
            370                 375                 380

<210> SEQ ID NO 2
<211> LENGTH: 1152
<212> TYPE: DNA
<213> ORGANISM: Corynebacterium glutamicum

<400> SEQUENCE: 2
atgtccagcg ccacaaccac tgatgttcgc aaagggctct acggagtcat cgccgattac      60
acggccgttt ccaaagtcat gccagagacc aattcactga cctaccgtgg ctacgcggtg     120
gaagatttgg tggaaaactg cagcttcgag gaggtgtttt acctcctgtg gcacggcgag     180
ctgcccactg cgcaacaact tgcggagttc aatgagcgtg gccgttccta ccgctccctg     240
gatgccggtt tgatctccct gatccactct ttgcccaaag aagcccaccc gatggatgtt     300
atgcgcaccg cggtgtccta catgggcacc aaggattccg agtatttcac caccgattct     360
gagcacatcc gcaaagttgg ccacaccttg ttggcgcagc ttccgatggt gctagccatg     420
gatattcgtc gccgcaaggg cctcgatatc atcgccctg actccagcaa gtcagtcgcc     480
gaaaacctgc tgtctatggt gtttggtact ggcccggaat cacctgcatc caacccagct     540
gacgtccgcg attttgagaa atcactgatc ctctacgccg agcactcctt caacgcctcc     600
accttcaccg cccgcgtgat cacctccacc aaatcggatg tgtactccgc aatcaccggc     660
gcgatcggtg ctctcaaggg cccattgcac ggtggcgcca acgagtttgt catgcacacc     720
atgttggcga tcgacgatcc aacaaggcc gccgctgga tcaacaacgc tttgacaac      780 aagaatgtgg tcatgggctt tggccaccgc gtgtacaagc gcggcgattc ccgcgtgcca     840
tcaatggaga agtccttccg ggaattagct gccgccacg acggcgaaaa gtgggttgcc     900
atgtatgaaa acatgcgcga cgccatggac gcccgcaccg gcatcaagcc gaatctcgat     960
ttccctgctg gccctgccta ccacctgctc ggtttcccgg tcgatttctt caccccgctg    1020
ttcgtcatcg cccgcgtcgc cggctggacg gcccacatcg tggagcagta cgaaaacaac    1080
tcgctcatcc gcccactgtc cgagtacaac ggcgaggagc agcgcgaggt cgcgcccatt    1140
gaaaagcgct aa                                                        1152

<210> SEQ ID NO 3
<211> LENGTH: 160
<212> TYPE: PRT
<213> ORGANISM: Corynebacterium glutamicum
```

<400> SEQUENCE: 3

```
Met Ala Ile Lys Leu Ser Ile Asp Leu Ser Asp Ala Thr Phe Ala Glu
1               5                   10                  15
Leu Ser Ala Val Ile Gly Tyr Ala His Gln Leu Gly Val Asp Ala Asp
            20                  25                  30
Glu Lys Leu Thr Phe Glu Gly Thr Val Leu Asn Ile Glu Phe Asp Gly
        35                  40                  45
Asp Leu Gln Phe Asp Asp Val Phe Asp Ala Phe Asp Glu Ala Glu Ile
    50                  55                  60
Glu Leu Asp Asn Pro Arg Glu Asp Gly Pro Ile Tyr Ala Asp Asp Leu
65                  70                  75                  80
Ile Asp Glu Asp Glu Asp Tyr Arg Ala Gln Thr Lys Ser Gln Ile Asn
                85                  90                  95
Asp Glu Val Ile Asn Glu Ile Arg Asp Gly Ile Ser Ser Phe Val Asp
            100                 105                 110
Gly Ile Val Asn Gly Leu Gly Gln Gly Arg Arg Gly Gly Arg Tyr Gly
            115                 120                 125
Asp Phe Gly Gly Pro Arg Gly Pro Arg Gly Pro Arg Asn Asp Gly Pro
        130                 135                 140
Phe Gly Pro Phe Gly Pro Phe Gly Pro Gly Tyr Arg Gly Pro Arg Phe
145                 150                 155                 160
```

<210> SEQ ID NO 4
<211> LENGTH: 483
<212> TYPE: DNA
<213> ORGANISM: Corynebacterium glutamicum

<400> SEQUENCE: 4

```
atggcaatca agctgtccat tgacctatca gatgcaacat tcgcagaact ttcggcagtc    60
atcggttacg cacatcagtt gggtgttgat gcggatgaga agctcacctt tgaaggtaca   120
gtccttaaca ttgaattcga cggcgacctt cagtttgatg atgtttttga tgcctttgat   180
gaggcggaaa ttgagctcga caaccctcgc gaagacggcc ccatctacgc agatgatctg   240
atcgatgagg atgaggacta ccgcgcacag accaagagcc agatcaacga cgaggttatc   300
aacgagatcc gcgatggtat ttcaagcttc gttgatggca tcgtaaatgg ccttggccag   360
ggtcgccgcg gtggacgtta cggtgatttc ggtgggccac gcggccctcg cggtccacgc   420
aatgacggtc cattcggccc atttggacca ttcggtccgg ataccgcgg tccgcgtttc    480
tag                                                                 483
```

<210> SEQ ID NO 5
<211> LENGTH: 1563
<212> TYPE: DNA
<213> ORGANISM: Corynebacterium glutamicum

<400> SEQUENCE: 5

```
atgagcgatg atcgtaaggc aattaaacgc gcactaatta gcgtgtatga caagactggc    60
ctggaggatc tagcccaggc acttcaccgc gagaacgtgg aaattgtttc caccggatcc   120
actgcggcga agattgctga gcttggtatt cctgttaccc cggttgagga gctcaccggt   180
ttccctgagt gccttgaggg ccgtgtgaag acactgcacc ctaaggttca cgctggcatc   240
ttggcggaca cccgcaagga agaccacctg cgtcagctca aggaacttga ggtcgcccca   300
ttccagcttg tcgtggtgaa cctgtaccca tttgctgaga ccgttgcgtc cggcgccgat   360
ttcgatgctt gcgttgagca gatcgacatc ggaggcccat ccatggttcg tgctgcggca   420
```

-continued

| | |
|---|---|
| aagaaccacc catctgtcgc tgtggttgtt tcaccgaacc gctacgagga tgtccaggaa | 480 |
| gctttgaaga ccggtggatt ctcccgcgcg gagcgcacca agttggctgc tgaggctttc | 540 |
| cgccacaccg caacctacga tgtcaccgtt gcaacctgga tgagcgagca gctggctgcc | 600 |
| gaagattctg agactgagtt cccaggttgg atcggcacca ccaacacctt gtcccgcagc | 660 |
| ttgcgttacg gtgagaaccc tcaccagtct gcagctttgt acgtgggcaa cacccgcgga | 720 |
| cttgcacagg ctaagcagtt ccacggcaag gaaatgagct acaacaacta caccgattct | 780 |
| gatgctgcat ggcgtgcagc gtgggatcac gagcgtcctt gtgtagctat catcaagcat | 840 |
| gcaaacccct tgtggcattg ctgtttctga tgagtccatc gcagcggcac ccgcgaggca | 900 |
| cacgcatgtg actctgtgtc cgcattcggt ggcgtcatcg cgtccaaccg tgaagtcagc | 960 |
| gttgagatgg ctaaccaggt tgcagagatc ttcactgagg tcatcatcgc tccttcctat | 1020 |
| gaagagggcg ctgtggagat cctgagccag aagaagaaca tccgtattct tcaggctgaa | 1080 |
| gcacctgtgc gtaagggctt tgagtcccgt gagatctccg gcggtctgct tgttcaggaa | 1140 |
| cgcgacttga tccacgctga gggcgacaac tccgcaaact ggactcttgc tgccggctct | 1200 |
| gctgtttctc ctgaggttct gaaggacctg gagttcgcgt ggactgcagt tcgttccgtg | 1260 |
| aagtccaacg caattctgtt ggctaagaac ggcgctaccg ttggcgttgg catgggacag | 1320 |
| gtcaaccgcg ttgactctgc tcgcttggct gtcgaccgtg caggtgcaga gcgcgctacc | 1380 |
| ggttccgttg ctgcttccga tgcgttcttc ccattcgctg acggctttga ggttctcgct | 1440 |
| gaggctggca tcactgctgt tgtgcagcct ggtggatcca ttcgcgacaa cgaggtcatt | 1500 |
| gaggcagcca acaaggctgg cgtgaccatg tacctgactg gtgcgcgaca cttcgctcac | 1560 |
| taa | 1563 |

<210> SEQ ID NO 6
<211> LENGTH: 603
<212> TYPE: DNA
<213> ORGANISM: Corynebacterium glutamicum

<400> SEQUENCE: 6

| | |
|---|---|
| atggctgtat acgaactccc agaactcgac tacgcatacg acgctctcga gccacacatc | 60 |
| gccgctgaaa tcatggagct tcaccactcc aagcaccacg caacctacgt tgcaggcgca | 120 |
| aatgcagcac tcgaggcact agagaaggca cgcgaagagg gcaccaaccc tgaccagatc | 180 |
| cgcgcactgt ccaagaacct tgcattcaac ctcggtggac acaccaacca ctccgttttc | 240 |
| tggaagaacc tctcccctaa cggtggtggc gagcctaccg gcgaactggc tgaggctatc | 300 |
| aaccgcgact tcggttcttt cgctaagttc caggatcact tcaactccgc agcactcggc | 360 |
| ctgcagggct ccggctgggc agttctcggc tacgaccaca tctccggtcg cctggttatc | 420 |
| gagcagctca ccgaccagca gggcaacatc tccgtcgaca tcaccccagt tctgatgctc | 480 |
| gatatgtggg agcacgcttt ctacctgcag tacaagaacg ttaaggcaga ttacgtcaag | 540 |
| gctgtttgga acgtcttcaa ctgggacgac gcagcagcac gcttcgcagc agcttccaag | 600 |
| taa | 603 |

<210> SEQ ID NO 7
<211> LENGTH: 371
<212> TYPE: PRT
<213> ORGANISM: Clostridium kluyveri

<400> SEQUENCE: 7

```
Met Gln Leu Phe Lys Leu Lys Ser Val Thr His His Phe Asp Thr Phe
 1               5                  10                  15

Ala Glu Phe Ala Lys Glu Phe Cys Leu Gly Glu Arg Asp Leu Val Ile
            20                  25                  30

Thr Asn Glu Phe Ile Tyr Glu Pro Tyr Met Lys Ala Cys Gln Leu Pro
             35                  40                  45

Cys His Phe Val Met Gln Glu Lys Tyr Gly Gln Gly Glu Pro Ser Asp
         50                  55                  60

Glu Met Met Asn Asn Ile Leu Ala Asp Ile Arg Asn Ile Gln Phe Asp
 65                  70                  75                  80

Arg Val Ile Gly Ile Gly Gly Thr Val Ile Asp Ile Ser Lys Leu
                 85                  90                  95

Phe Val Leu Lys Gly Leu Asn Asp Val Leu Asp Ala Phe Asp Arg Lys
             100                 105                 110

Ile Pro Leu Ile Lys Glu Lys Glu Leu Ile Ile Val Pro Thr Thr Cys
             115                 120                 125

Gly Thr Gly Ser Glu Val Thr Asn Ile Ser Ile Ala Glu Ile Lys Ser
         130                 135                 140

Arg His Thr Lys Met Gly Leu Ala Asp Ala Ile Val Ala Asp His
145                 150                 155                 160

Ala Ile Ile Ile Pro Glu Leu Leu Lys Ser Leu Pro Phe His Phe Tyr
                 165                 170                 175

Ala Cys Ser Ala Ile Asp Ala Leu Ile His Ala Ile Glu Ser Tyr Val
             180                 185                 190

Ser Pro Lys Ala Ser Pro Tyr Ser Arg Leu Phe Ser Glu Ala Ala Trp
         195                 200                 205

Asp Ile Ile Leu Glu Val Phe Lys Lys Ile Ala Glu His Gly Pro Glu
         210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                 245                 250                 255

Tyr Pro Leu Gly Gly Asn Tyr His Val Pro His Gly Glu Ala Asn Tyr
             260                 265                 270

Gln Phe Phe Thr Glu Val Phe Lys Val Tyr Gln Lys Lys Asn Pro Phe
             275                 280                 285

Gly Tyr Ile Val Glu Leu Asn Trp Lys Leu Ser Lys Ile Leu Asn Cys
         290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Val
                 325                 330                 335

Arg Gly Phe Ala Glu Ser Val Leu Lys Thr Gln Gln Arg Leu Leu Ala
             340                 345                 350

Asn Asn Tyr Val Glu Leu Thr Val Asp Glu Ile Glu Gly Ile Tyr Arg
         355                 360                 365

Arg Leu Tyr
     370
```

<210> SEQ ID NO 8
<211> LENGTH: 431
<212> TYPE: PRT
<213> ORGANISM: Porphyromonas gingivalis

<400> SEQUENCE: 8

```
Met Lys Asp Val Leu Ala Glu Tyr Ala Ser Arg Ile Val Ser Ala Glu
  1               5                  10                  15

Glu Ala Val Lys His Ile Lys Asn Gly Glu Arg Val Ala Leu Ser His
             20                  25                  30

Ala Ala Gly Val Pro Gln Ser Cys Val Asp Ala Leu Val Gln Gln Ala
             35                  40                  45

Asp Leu Phe Gln Asn Val Glu Ile Tyr His Met Leu Cys Leu Gly Glu
         50                  55                  60

Gly Lys Tyr Met Ala Pro Glu Met Ala Pro His Phe Arg His Ile Thr
 65              70                  75                  80

Asn Phe Val Gly Gly Asn Ser Arg Lys Ala Val Glu Glu Asn Arg Ala
                 85                  90                  95

Asp Phe Ile Pro Val Phe Phe Tyr Glu Val Pro Ser Met Ile Arg Lys
             100                 105                 110

Asp Ile Leu His Ile Asp Val Ala Ile Val Gln Leu Ser Met Pro Asp
             115                 120                 125

Glu Asn Gly Tyr Cys Ser Phe Gly Val Ser Cys Asp Tyr Ser Lys Pro
         130                 135                 140

Ala Ala Glu Ser Ala His Leu Val Ile Gly Ile Asn Arg Gln Met
145                 150                 155                 160

Pro Tyr Val His Gly Asp Asn Leu Ile His Ile Ser Lys Leu Asp Tyr
             165                 170                 175

Ile Val Met Ala Asp Tyr Pro Ile Tyr Ser Leu Ala Lys Pro Lys Ile
             180                 185                 190

Gly Glu Val Glu Glu Ala Ile Gly Arg Asn Cys Ala Glu Leu Ile Glu
             195                 200                 205

Asp Gly Ala Thr Leu Gln Leu Gly Ile Gly Ala Ile Pro Asp Ala Ala
210                 215                 220

Leu Leu Phe Leu Lys Asp Lys Asp Leu Gly Ile His Thr Glu Met
225                 230                 235                 240

Phe Ser Asp Gly Val Val Glu Leu Val Arg Ser Gly Val Ile Thr Gly
             245                 250                 255

Lys Lys Lys Thr Leu His Pro Gly Lys Met Val Ala Thr Phe Leu Met
             260                 265                 270

Gly Ser Glu Asp Val Tyr His Phe Ile Asp Lys Asn Pro Asp Val Glu
         275                 280                 285

Leu Tyr Pro Val Asp Tyr Val Asn Asp Pro Arg Val Ile Ala Gln Asn
         290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
             325                 330                 335

Gly Gln Val Asp Tyr Val Arg Gly Ala Ala Trp Ser Lys Asn Gly Lys
             340                 345                 350

Ser Ile Met Ala Ile Pro Ser Thr Ala Lys Asn Gly Thr Ala Ser Arg
             355                 360                 365

Ile Val Pro Ile Ile Ala Glu Gly Ala Ala Val Thr Thr Leu Arg Asn
             370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
             405                 410                 415
```

```
Asp Phe Arg Glu Glu Leu Thr Lys His Leu Arg Lys Arg Phe Gly
            420                 425                 430
```

<210> SEQ ID NO 9
<211> LENGTH: 858
<212> TYPE: PRT
<213> ORGANISM: Clostridium acetobutyricum

<400> SEQUENCE: 9

```
Met Lys Val Thr Asn Gln Lys Glu Leu Lys Gln Lys Leu Asn Glu Leu
  1               5                  10                  15

Arg Glu Ala Gln Lys Lys Phe Ala Thr Tyr Thr Gln Glu Gln Val Asp
             20                  25                  30

Lys Ile Phe Lys Gln Cys Ala Ile Ala Ala Lys Glu Arg Ile Asn
         35                  40                  45

Leu Ala Lys Leu Ala Val Glu Glu Thr Gly Ile Gly Leu Val Glu Asp
     50                  55                  60

Lys Ile Ile Lys Asn His Phe Ala Ala Glu Tyr Ile Tyr Asn Lys Tyr
 65                  70                  75                  80

Lys Asn Glu Lys Thr Cys Gly Ile Ile Asp His Asp Asp Ser Leu Gly
                 85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
            115                 120                 125

Lys Thr Arg Asn Ala Ile Phe Phe Ser Pro His Pro Arg Ala Lys Lys
        130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365
```

```
Leu Tyr Ile Asp Ser Gln Asn Asn Lys Asp Lys Val Lys Glu Phe Gly
        370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510

Asp Ile Lys Ser Asp Pro Thr Ile Asp Ser Val Lys Lys Gly Ala Lys
            515                 520                 525

Glu Met Leu Asn Phe Glu Pro Asp Thr Ile Ile Ser Ile Gly Gly Gly
        530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
                660                 665                 670

Ala Leu Arg Ala Ile Lys Met Ile Phe Lys Tyr Leu Pro Arg Ala Tyr
            675                 680                 685

Lys Asn Gly Thr Asn Asp Ile Glu Ala Arg Glu Lys Met Ala His Ala
        690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
                740                 745                 750

Asp Cys Pro Thr Lys Gln Thr Ala Phe Pro Gln Tyr Lys Ser Pro Asn
            755                 760                 765

Ala Lys Arg Lys Tyr Ala Glu Ile Ala Glu Tyr Leu Asn Leu Lys Gly
        770                 775                 780
```

```
Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
            805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
            835                 840                 845

Glu Leu Lys Asp Ile Tyr Ile Lys Ser Phe
    850                 855
```

<210> SEQ ID NO 10
<211> LENGTH: 451
<212> TYPE: PRT
<213> ORGANISM: Porphyromonas gingivalis

<400> SEQUENCE: 10

```
Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
            35                  40                  45

Val Asp Glu Thr Gly Met Gly Val Tyr Glu His Lys Val Ala Lys Asn
    50                  55                  60

Gln Gly Lys Ser Lys Gly Val Trp Tyr Asn Leu His Asn Lys Lys Ser
65              70                  75                  80

Ile Gly Ile Leu Asn Ile Asp Glu Arg Thr Gly Met Ile Glu Ile Ala
                85                  90                  95

Lys Pro Ile Gly Val Val Gly Ala Val Thr Pro Thr Thr Asn Pro Ile
            100                 105                 110

Val Thr Pro Met Ser Asn Ile Ile Phe Ala Leu Lys Thr Cys Asn Ala
            115                 120                 125

Ile Ile Ile Ala Pro His Pro Arg Ser Lys Lys Cys Ser Ala His Ala
130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
            165                 170                 175

Met Gly Ala Val Asp Val Val Val Ala Thr Gly Gly Met Gly Met Val
            180                 185                 190

Lys Ser Ala Tyr Ser Ser Gly Lys Pro Ser Phe Gly Val Gly Ala Gly
            195                 200                 205

Asn Val Gln Val Ile Val Asp Ser Asn Ile Asp Phe Glu Ala Ala Ala
    210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
                245                 250                 255

Thr Ala Phe Arg Asn His Gly Ala Tyr Phe Cys Asp Glu Ala Glu Gly
            260                 265                 270

Asp Arg Ala Arg Ala Ala Ile Phe Glu Asn Gly Ala Ile Ala Lys Asp
            275                 280                 285

Val Val Gly Gln Ser Val Ala Phe Ile Ala Lys Lys Ala Asn Ile Asn
    290                 295                 300
```

Ile Pro Glu Gly Thr Arg Ile Leu Val Val Glu Ala Arg Gly Val Gly
305                 310                 315                 320

Ala Glu Asp Val Ile Cys Lys Glu Lys Met Cys Pro Val Met Cys Ala
                325                 330                 335

Leu Ser Tyr Lys His Phe Glu Glu Gly Val Glu Ile Ala Arg Thr Asn
            340                 345                 350

Leu Ala Asn Glu Gly Asn Gly His Thr Cys Ala Ile His Ser Asn Asn
        355                 360                 365

Gln Ala His Ile Ile Leu Ala Gly Ser Glu Leu Thr Val Ser Arg Ile
370                 375                 380

Val Val Asn Ala Pro Ser Ala Thr Thr Ala Gly Gly His Ile Gln Asn
385                 390                 395                 400

Gly Leu Ala Val Thr Asn Thr Leu Gly Cys Gly Ser Trp Gly Asn Asn
                405                 410                 415

Ser Ile Ser Glu Asn Phe Thr Tyr Lys His Leu Leu Asn Ile Ser Arg
            420                 425                 430

Ile Ala Pro Leu Asn Ser Ser Ile His Ile Pro Asp Lys Glu Ile
        435                 440                 445

Trp Glu Leu
    450

<210> SEQ ID NO 11
<211> LENGTH: 538
<212> TYPE: PRT
<213> ORGANISM: Clostridium kluyveri

<400> SEQUENCE: 11

Met Ser Lys Gly Ile Lys Asn Ser Gln Leu Lys Lys Asn Val Lys
1               5                   10                  15

Ala Ser Asn Val Ala Glu Lys Ile Glu Glu Lys Val Glu Lys Thr Asp
                20                  25                  30

Lys Val Val Glu Lys Ala Ala Glu Val Thr Glu Lys Arg Ile Arg Asn
            35                  40                  45

Leu Lys Leu Gln Glu Lys Val Val Thr Ala Asp Val Ala Ala Asp Met
        50                  55                  60

Ile Glu Asn Gly Met Ile Val Ala Ile Ser Gly Phe Thr Pro Ser Gly
65                  70                  75                  80

Tyr Pro Lys Glu Val Pro Lys Ala Leu Thr Lys Lys Val Asn Ala Leu
                85                  90                  95

Glu Glu Glu Phe Lys Val Thr Leu Tyr Thr Gly Ser Ser Thr Gly Ala
            100                 105                 110

Asp Ile Asp Gly Glu Trp Ala Lys Ala Gly Ile Ile Glu Arg Arg Ile
        115                 120                 125

Pro Tyr Gln Thr Asn Ser Asp Met Arg Lys Lys Ile Asn Asp Gly Ser
130                 135                 140

Ile Lys Tyr Ala Asp Met His Leu Ser His Met Ala Gln Tyr Ile Asn
145                 150                 155                 160

Tyr Ser Val Ile Pro Lys Val Asp Ile Ala Ile Glu Ala Val Ala
                165                 170                 175

Ile Thr Glu Glu Gly Asp Ile Ile Pro Ser Thr Gly Ile Gly Asn Thr
            180                 185                 190

Ala Thr Phe Val Glu Asn Ala Asp Lys Val Ile Val Glu Ile Asn Glu
        195                 200                 205

Ala Gln Pro Leu Glu Leu Glu Gly Met Ala Asp Ile Tyr Thr Leu Lys

```
                210                215                220
Asn Pro Pro Arg Arg Glu Pro Ile Pro Ile Val Asn Ala Gly Asn Arg
225                230                235                240

Ile Gly Thr Thr Tyr Val Thr Cys Gly Ser Glu Lys Ile Cys Ala Ile
                245                250                255

Val Met Thr Asn Thr Gln Asp Lys Thr Arg Pro Leu Thr Glu Val Ser
                260                265                270

Pro Val Ser Gln Ala Ile Ser Asp Asn Leu Ile Gly Phe Leu Asn Lys
            275                280                285

Glu Val Glu Glu Gly Lys Leu Pro Lys Asn Leu Leu Pro Ile Gln Ser
290                295                300

Gly Val Gly Ser Val Ala Asn Ala Val Leu Ala Gly Leu Cys Glu Ser
305                310                315                320

Asn Phe Lys Asn Leu Ser Cys Tyr Thr Glu Val Ile Gln Asp Ser Met
                325                330                335

Leu Lys Leu Ile Lys Cys Gly Lys Ala Asp Val Val Ser Gly Thr Ser
                340                345                350

Ile Ser Pro Ser Pro Glu Met Leu Pro Glu Phe Ile Lys Asp Ile Asn
                355                360                365

Phe Phe Arg Glu Lys Ile Val Leu Arg Pro Gln Glu Ile Ser Asn Asn
            370                375                380

Pro Glu Ile Ala Arg Arg Ile Gly Val Ile Ser Ile Asn Thr Ala Leu
385                390                395                400

Glu Val Asp Ile Tyr Gly Asn Val Asn Ser Thr His Val Met Gly Ser
                405                410                415

Lys Met Met Asn Gly Ile Gly Gly Ser Gly Asp Phe Ala Arg Asn Ala
                420                425                430

Tyr Leu Thr Ile Phe Thr Thr Glu Ser Ile Ala Lys Lys Gly Asp Ile
                435                440                445

Ser Ser Ile Val Pro Met Val Ser His Val Asp His Thr Glu His Asp
            450                455                460

Val Met Val Ile Val Thr Glu Gln Gly Val Ala Asp Leu Arg Gly Leu
465                470                475                480

Ser Pro Arg Glu Lys Ala Val Ala Ile Ile Glu Asn Cys Val His Pro
                485                490                495

Asp Tyr Lys Asp Met Leu Met Glu Tyr Phe Glu Glu Ala Cys Lys Ser
                500                505                510

Ser Gly Gly Asn Thr Pro His Asn Leu Glu Lys Ala Leu Ser Trp His
            515                520                525

Thr Lys Phe Ile Lys Thr Gly Ser Met Lys
530                535

<210> SEQ ID NO 12
<211> LENGTH: 1116
<212> TYPE: DNA
<213> ORGANISM: Clostridium kluyveri

<400> SEQUENCE: 12
atgcagcttt tcaagctcaa gagcgtcaca catcactttg atactttgc agagtttgcc      60 aaggagttct gtctcggtga acgcgacttg gtaattacca acgagttcat ctacgaaccg     120
tatatgaagg catgccagct gccttgtcat tttgtgatgc aggagaaata cggccaaggc     180
gagccttctg acgagatgat gaacaacatc ctagcagata tccgtaatat ccagttcgac     240
cgcgtgatcg ggatcggagg tggtacggtt attgacatct caaaactctt tgttctgaag     300
```

```
ggattaaatg atgttctcga cgcgttcgat cgcaagattc ccctatcaa agagaaagaa      360 ctgatcattg tgcccaccac ctgcggaacc ggctcggagg tgacgaacat ttccatcgcc      420
gagatcaagt cccggcacac caagatgggt ttggctgacg atgcaattgt tgctgaccac      480
gccataatca tccctgaact tctgaagagc ttgcccttcc acttctatgc atgctccgca      540
atcgacgctc ttattcatgc catcgagtca tacgtttctc aaaagcgtc tccatactcc      600 cgtctgttca gtgaggcggc gtgggacatt atcctggaag ttttcaagaa aatcgccgaa      660
cacggcccag agtaccgctt cgagaagctg ggggaaatga tcatggccag caactatgcc      720
ggtatcgctt tcggcaacgc aggcgttggc gccgtccacg ctctatccta cccgttgggc      780
ggcaactatc acgtgccgca tggagaagca aactatcagt tcttcaccga ggtctttaaa      840
gtataccaaa agaagaatcc gttcggctat attgtcgaac tcaactggaa gctctccaag      900
attctgaact gccagccaga gtacgtgtac ccgaagctgg atgaactgct cggttgcctt      960
cttaccaaga aacctttgca cgaatacggc atgaaggacg aagaggttcg tggcttcgcg     1020
gaatcggtcc tgaagaccca gcaacgcttg ctcgccaaca actacgtcga acttactgtc     1080
gatgagatcg aaggtatcta ccgacgtctc tactag                              1116

<210> SEQ ID NO 13
<211> LENGTH: 1296
<212> TYPE: DNA
<213> ORGANISM: Porphyromonas gingivalis

<400> SEQUENCE: 13
atgaaggatg tactggcgga atacgcctcc cgcattgttt cggcggagga ggccgttaag       60
cacatcaaaa acggtgaacg ggtagctttg tcacacgctg ccggcgtgcc tcagagttgc      120
gttgacgcac tggtgcagca ggccgacctt ttccagaatg tggaaatcta tcacatgctg      180
tgcctcggtg agggtaagta tatggcgcct gagatggccc ctcacttccg ccacatcacc      240
aactttgtcg gtggtaactc ccgtaaggcg gtcgaagaaa accgggccga tttcattccg      300
gtattctttt acgaggtgcc aagcatgatt cgcaaagaca tcctccacat tgatgtcgcc      360
atcgttcagc tttcaatgcc tgacgaaaat ggttactgtt cctttggagt atcttgcgat      420
tactccaagc cggcagcaga gagcgctcac ctggttatcg agaaatcaa ccgtcaaatg      480 ccatacgtac acgcgacaa cttgattcat atctccaagt tggattacat cgtgatggca      540
gactacccca tctactctct tgcaaagccc aagatcgggg aagtcgagga agctatcggg      600
aggaattgtg ccgagcttat tgaagatggt gccactctcc agctgggaat cggcgcgatt      660
cctgatgcgg ccctgttatt tctcaaggac aaaaaggatc tgggcatcca taccgaaatg      720
ttctccgatg gtgttgtcga attggttcgc tccggcgtta tcacaggcaa gaaaaagact      780
cttcaccccg gaaagatggt cgcaaccttc ctgatgggaa gcgaggacgt gtatcatttc      840
atcgataaaa accccgatgt agaactgtat ccagtagatt acgtgaatga cccgcgtgtg      900
atcgcccaaa acgacaatat ggtctcgatt aacagctgca tcgaaatcga ccttatggga      960
caggtcgtgt ccgagtgcat cggctcaaag caattcagcg gcaccggcgg ccaagttgac     1020
tacgtgcgtg gcgcagcatg gtctaaaaac ggcaaatcga tcatggcaat cccgtccact     1080
gcaaaaaacg gtacggcatc tcgaattgta cctatcatcg cggagggcgc tgctgtcacc     1140
accctgcgca acgaggtcga ttacgttgta accgagtacg gtatcgctca gctcaagggc     1200
aagagcctgc gccagcgcgc agaggctttg atcgcgatag cccaccccga cttccgtgag     1260
```
gaactaacga aacatctccg caagcgattc ggataa                        1296

<210> SEQ ID NO 14
<211> LENGTH: 2577
<212> TYPE: DNA
<213> ORGANISM: Clostridium acetobutyricum

<400> SEQUENCE: 14
atgaaagtaa ccaatcagaa agagttgaag cagaagttga acgagctgcg agaggctcag    60
aagaagttcg caacctacac ccaggaacag gtggacaaga tctttaagca gtgtgccatt   120
gcagccgcga aagaacgtat taatctcgcg aaacttgcgg tcgaggaaac cggtattggg   180
ctggtagaag acaagatcat caagaaccac ttcgccgctg aatacatcta caacaagtac   240
aaaaacgaaa agacatgtgg tatcatcgac cacgacgaca gcttgggcat caccaaggta   300
gcggagccaa tcggtatcgt cgcagctatc gtgcccacta ctaaccctac ctccactgct   360
attttcaagt cactcatctc cctgaaaacc cgcaatgcta tcttcttctc acctcaccca   420
cgcgctaaga aatcaactat cgctgcagct aaacttatcc tggatgcagc cgtgaaagcc   480
ggggctccga aaacatcat cggttggatc gacgaacctt ccattgaact ctctcaagac   540
ctcatgtccg aggcagacat tatcctggca accggaggcc catccatggt taaagcagct   600
tacagctcag gcaagccggc tatcggcgtt ggagctggta acactccagc aatcatcgac   660
gagtcggccg atatcgacat ggcagtgtcc tctattatcc tgtccaaaac ttatgacaac   720
ggcgttattt gcgcgtccga gcagtctatt ctcgtcatga actctattta cgagaaggta   780
aaggaggagt ttgtgaagcg ggggtcgtac attctgaacc agaacgagat cgctaagatc   840
aaagagacta tgtttaaaaa cggagccatc aacgcagata tcgtagggaa gtccgcgtac   900
atcattgcta gatggctgg aatcgaagtc cctcaaacca cgaaaattct gatcggcgag   960
gtgcaatcgg tcgaaaagtc cgagctgttc tcgcatgaaa agttgtcccc ggtcctcgcg  1020
atgtataaag ttaaggattt tgatgaagca ctcaagaaag ctcagcgcct gatcgaattg  1080
ggtggctcgg gtcacaccct ctttcctcta cattgactcc cagaacaataa agataaggtg  1140
aaagagttcg gcctggctat gaagacgtct cgtaccttca tcaatatgcc ctcttcacag  1200
ggcgccagcg gtgaccttta caatttcgct atcgctccta gctttaccct cggctgcggc  1260
acctggggcg gtaattctgt gtcccaaaac gtcgaaccaa agcatctgct caacattaaa  1320
agcgtcgccg aacgtcgcga gaacatgttg tggttcaagg tcccgcaaaa aatctacttc  1380
aagtatggtt gcttgcgctt tgcacttaaa gagcttaagg acatgaataa aaagcgggcg  1440
ttcatcgtca ctgataagga tctgttcaaa ctgggctatg ttaacaagat taccaaggtc  1500
ctggatgaga tcgatatcaa gtattccatc ttcaccgata ttaagtccga tccgaccatt  1560
gattccgtga agaagggcgc gaaggagatg ctcaactttg aacccgacac gattatttct  1620
attggcggag gcagcccaat ggacgcagct aaggttatgc acctgctgta tgagtaccca  1680
gaagcagaga tcgagaacct tgcaatcaat ttcatggata ttcgcaaacg catttgcaac  1740
tttcctaagc ttggtacaaa agctatctct gttgcgatcc ctaccaccgc aggaaccggc  1800
agcgaagcga caccattcgc cgttattacc aacgatgaaa caggtatgaa gtacccactt  1860
acctcttatg aacttacccc gaacatggct atcattgata cggaattgat gctgaacatg  1920
ccgcgcaagt tgaccgcagc tacgggaatc gatgcattgg ttcatgcaat cgaggcatac  1980
gtttccgtca tggcaaccga ttacaccgac gagctcgcgt tgcgtgcgat taaaatgatc  2040
ttcaagtacc ttccacgcgc atacaagaat ggcacaaacg atattgaagc ccgagaaaag  2100

```
atggcacacg cttcgaacat cgctggtatg gccttcgcga atgcgtttct cggagtgtgt    2160
cactccatgg cgcacaaact gggagccatg catcacgtgc cccacggtat cgcatgcgcc    2220
gttcttattg aagaggtgat caagtataat gccaccgatt gccccactaa gcagacggcc    2280
ttccctcagt acaaatcgcc caatgccaag cgtaaatacg cggaaattgc cgagtacttg    2340
aaccttaagg ggaccagcga cacggaaaag gtgaccgcac tgattgaagc catctccaag    2400
cttaagatcg acctgagcat cccacaaaac atctcagcag ccggcattaa caagaaggac    2460
ttctacaaca ctctcgacaa gatgtcagag ctcgccttcg atgatcagtg cactaccgca    2520
aacccacgtt atccgctcat ctctgaactg aaggatatct acatcaagtc gttttaa       2577
```

<210> SEQ ID NO 15
<211> LENGTH: 1356
<212> TYPE: DNA
<213> ORGANISM: Porphyromonas gingivalis

<400> SEQUENCE: 15

```
atggagatta aagagatggt cagtcttgcg cgcaaagctc agaaggagta tcaggccacc      60
cataaccaag aagctgtgga caacatctgc cgagcagcag cgaaggttat ttacgaaaat    120
gcagcaattc tggcacgcga ggcagtggac gaaaccggca tgggtgttta cgagcacaag    180
gtggccaaga tcaaggcaa gtccaaaggt gtttggtaca acctgcataa caagaagtcg    240
attggcatcc tcaatatcga cgagcgtacc ggcatgatcg agatcgcaaa acctatcggg    300
gttgtaggcg ccgttacgcc aaccaccaac cctatcgtta ctccgatgag caacatcatc    360
tttgctctta agacctgcaa cgccatcatt atcgcccac acccgcgctc caaaaagtgc    420
tctgcccacg cagttcggct gatcaaagag gctatcgctc cgttcaacgt gcccgaaggt    480
atggttcaga tcatcgagga gcctagcatc gagaagacgc aggaattgat gggcgccgta    540
gacgtggtcg ttgctaccgg gggcatgggc atggtcaagt ctgcctactc ctcagggaag    600
ccttctttcg gtgtcggagc cggcaatgtt caggtgatag tggacagcaa catcgacttc    660
gaagcggcag cagaaaagat catcaccgga cgtgccttcg acaacggtat catctgctca    720
ggcgaacagt ccatcatcta caacgaggct gacaaggaag cagttttcac agcattccgc    780
aaccacggtg cgtacttttg cgacgaggcc gagggagatc gggctcgtgc agcgatcttc    840
gaaaatggag ccatcgcgaa agatgttgtg gccagtccg ttgcctttat tgcaaagaag    900
gcgaacatta atatccccga gggtactcgt attctcgtgg tcgaagctcg cggagtaggc    960
gccgaagatg tcatctgtaa agaaagatg tgtccagtca tgtgcgccct ctcctacaag    1020
cacttcgaag aggggtaga gatcgcaagg acgaacctcg caaacgaagg caatggccat    1080
acctgtgcta tccactccaa caaccaagca cacatcatct tggcaggctc ggagctgacc    1140
gtgtctcgca tcgtggtcaa cgcgccaagt gctaccacag caggcggtca catccagaac    1200
ggtcttgccg tcaccaatac tctaggctgc ggctcttggg gtaacaactc gatctccgaa    1260
aacttcactt ataaacacct gctcaacatt tcacgcatcg ccccgttgaa ctccagcatt    1320
catatcccag atgataagga aatctgggaa ctctaa                              1356
```

<210> SEQ ID NO 16
<211> LENGTH: 1617
<212> TYPE: DNA
<213> ORGANISM: Clostridium kluyveri

<400> SEQUENCE: 16

```
atgtctaaag gaatcaagaa tagccaattg aaaaaaaaga acgtcaaggc cagtaacgtt    60
gctgagaaga tcgaagagaa ggtggaaaag accgacaagg tcgttgagaa ggctgctgag   120
gtgaccgaaa agcgcattcg aaacttaaag ctccaggaaa aagttgtgac cgcagatgtc   180
gcagctgaca tgatcgagaa tggcatgatc gtcgcaatta gcggcttcac gccatccggg   240
tatccaaagg aggttccaaa agcccttact aagaaggtta atgcgctgga ggaggagttc   300
aaggtgacgc tgtataccgg ttctagcaca ggcgctgata ttgacggaga atgggcgaag   360
gcaggaataa tcgaacggcg tatcccatac cagaccaact ctgacatgag gaaaaaaata   420
aacgatggtt caatcaagta cgcagatatg cacctgagcc acatggctca atacattaac   480
tattctgtga ttcctaaggt tgacattgcc atcatcgagg cggtggccat taccgaggaa   540
ggggatatta ttcctagtac tggaatcggc aacacagcta cgtttgtcga aatgcggat    600
aaggtaattg tggaaataaa cgaggctcag ccgcttgagt tggaaggcat ggcagatatc   660
tataccctga agaaccctcc acgtcgcgag cccatcccga tagtcaacgc aggcaaccgc   720
atagggacca cttacgtcac ctgtggctct gaaaaaatct gcgcgatcgt catgaccaac   780
acccaagaca aaacccgccc actcaccgaa gtttctcctg tcagtcaggc aatctccgat   840
aacctgattg gcttcctgaa caaagaagta gaggagggta aactcccaaa aaacctgctc   900
cccatacagt caggtgtcgg ttcggttgct aaccgcgttc tagccggact ctgcgaatca   960
aacttcaaaa atttgagctg ctacacagaa gtgatccagg attcgatgtt gaagctcatc  1020
aaatgtggaa aggcagatgt ggtgtccggc acctcgatct cgccatcacc ggaaatgctg  1080
cccgagttca taaaggacat aaattttttt cgcgagaaga tagtactgcg cccccaggaa  1140
atatctaata atccggaaat agctcgtcgt ataggagtga tctccataaa cactgctttg  1200
gaagtagaca tctacggtaa tgtgaactcc acgcatgtca tgggctccaa gatgatgaac  1260
ggcatcggcg gcagcggcga ctttgcccgc aacgcatacc tcaccatatt cactacggag  1320
tccatcgcga agaagggcga catttcctct atcgttccta tggtttccca cgtgaccac   1380
accgagcatg acgtaatggt catcgttacc gaacaggggg ttgcggatct cgcggtctt   1440
tcccctcggg aaaaggccgt ggcgataatt gagaattgcg tccacccgga ttacaaggat  1500
atgctcatgg agtacttcga ggaggcttgt aagtcctcag gtggcaacac cccacacaac  1560
cttgaaaaag ccctatcctg gcacactaag ttcataaaaa ctggctcgat gaagtaa     1617
```

<210> SEQ ID NO 17
<211> LENGTH: 43
<212> TYPE: DNA
<213> ORGANISM: Artificial Sequence
<220> FEATURE:
<223> OTHER INFORMATION: Synthetic ldhA_5'_HindIII

<400> SEQUENCE: 17
catgattacg ccaagcttga gagcccacca cattgcgatt tcc                      43

<210> SEQ ID NO 18
<211> LENGTH: 42
<212> TYPE: DNA
<213> ORGANISM: Artificial Sequence
<220> FEATURE:
<223> OTHER INFORMATION: Synthetic ldhA_up_3'_XhoI

<400> SEQUENCE: 18
tcgaaactcg agtttcgatc ccacttcctg atttccctaa cc                       42

```
<210> SEQ ID NO 19
<211> LENGTH: 39
<212> TYPE: DNA
<213> ORGANISM: Artificial Sequence
<220> FEATURE:
<223> OTHER INFORMATION: Synthetic ldhA_dn_5'_XhoI

<400> SEQUENCE: 19
tcgaaactcg agtaaatctt tggcgcctag ttggcgacg                              39

<210> SEQ ID NO 20
<211> LENGTH: 46
<212> TYPE: DNA
<213> ORGANISM: Artificial Sequence
<220> FEATURE:
<223> OTHER INFORMATION: Synthetic ldhA_3'_EcoRI

<400> SEQUENCE: 20
acgacggcca gtgaattcga cgacatctga gggtggataa agtggg                      46

<210> SEQ ID NO 21
<211> LENGTH: 20
<212> TYPE: DNA
<213> ORGANISM: Artificial Sequence
<220> FEATURE:
<223> OTHER INFORMATION: Synthetic ldhA up

<400> SEQUENCE: 21
atcgggcata attaaaggtg                                                   20

<210> SEQ ID NO 22
<211> LENGTH: 22
<212> TYPE: DNA
<213> ORGANISM: Artificial Sequence
<220> FEATURE:
<223> OTHER INFORMATION: Synthetic ldhA down

<400> SEQUENCE: 22
gtcacctcat caagttctag aa                                                22

<210> SEQ ID NO 23
<211> LENGTH: 6702
<212> TYPE: DNA
<213> ORGANISM: Artificial Sequence
<220> FEATURE:
<223> OTHER INFORMATION: Synthetic 4gene_cat1_sucD_4hbd_cat2

<400> SEQUENCE: 23
tctagaatga ctattaatgt ctccgaacta cttgccaaag tccccacggg tctactgatt        60
ggtgattcct gggtggaagc atccgacggc ggtactttcg atgtggaaaa cccagcgacg       120
ggtgaaacaa tcgcaacgct cgcgtctgct acttccgagg atgcactggc tgctcttgat       180
gctgcatgcg ctgttcaggc cgagtgggct aggatgccag cgcgcgagcg ttctaatatt       240
ttacgccgcg gttttgagct cgtagcagaa cgtcagaaag agttcgccac cctcatgacc       300
ttggaaatgg gcaagccttt ggctgaagct cgcggcgaag tcacctacgg caacgaattc       360
ctgcgctggt tctctgagga agcagttcgt ctgtatggcc gttacggaac cacaccagaa       420
ggcaacttgc ggatgctgac cgccctcaag ccagttggcc cgtgcctcct gatcaccccca      480 tggaacttcc cactagcaat ggctactaga tgattttgca tctgctgcga aatctttgtt      540
tccccgctaa agttgaggac aggttgacac ggagttgact cgacgaatta tccaatgtga       600
gtaggtttgg tgcgtgagtt ggaaaaattc gccatactcg cccttgggtt ctgtcagctc       660
```

```
aagaattctt gagtgaccga tgctctgatt gacctaactg cttgacacat tgcatttcct    720
acaatcttta gaggagacac aacatgtcta aaggaatcaa gaatagccaa ttgaaaaaaa    780
agaacgtcaa ggccagtaac gttgctgaga agatcgaaga gaaggtggaa aagaccgaca    840
aggtcgttga gaaggctgct gaggtgaccg aaaagcgaat tcgaaactta agctccagg     900 aaaaagttgt gaccgcagat gtcgcagctg acatgatcga gaatggcatg atcgtcgcaa    960
ttagcggctt cacgccatcc gggtatccaa aggaggttcc aaaagccctt actaagaagg   1020
ttaatgcgct ggaggaggag ttcaaggtga cgctgtatac cggttctagc acaggcgctg   1080
atattgacgg agaatgggcg aaggcaggaa taatcgaacg gcgtatccca taccagacca   1140
actctgacat gaggaaaaaa ataaacgatg gttcaatcaa gtacgcagat atgcacctga   1200
gccacatggc tcaatacatt aactattctg tgattcctaa ggttgacatt gccatcatcg   1260
aggcggtggc cattaccgag gaaggggata ttattcctag tactggaatc ggcaacacag   1320
ctacgtttgt cgagaatgcg gataaggtaa ttgtggaaat aaacgaggct cagccgcttg   1380
agttggaagg catggcagat atctataccc tgaagaaccc tccacgtcgc gagcccatcc   1440
cgatagtcaa cgcaggcaac cgcataggga ccacttacgt cacctgtggc tctgaaaaaa   1500
tctgcgcgat cgtcatgacc aacacccaag acaaaacccg cccactcacc gaagtttctc   1560
ctgtcagtca ggcaatctcc gataacctga ttggcttcct gaacaaagaa gtagaggagg   1620
gtaaactccc aaaaaacctg ctccccatac agtcaggtgt cggttcggtt gctaacgccg   1680
tgcatcccgg actctgcgaa tcaaacttca aaaatttgag ctgctacaca gaagtgatcc   1740
aggattcgat gttgaagctg atcaaatgtg gaaaggcaga tgtggtgtcc ggcacctcga   1800
tctcgccatc accggaaatg ctgcccgagt tcataaagga cataaatttt tttcgcgaga   1860
agatagtact gcgcccccag gaaatatcta ataatccgga aatagctcgt cgtataggag   1920
tgatctccat aaacactgct ttggaagtag acatctacgg taatgtgaac tccacgcatg   1980
tcatgggctc caagatgatg aacggcatcg gcggcagcgg cgactttgcc cgcaacgcat   2040
acctcaccat attcactacg gagtccatcg cgaagaaggg cgacatttcc tctatcgttc   2100
ctatggtttc ccacgtggac cacaccgagc atgacgtaat ggtcatcgtt accgaacagg   2160
gggttgcgga tctccgcggt cttttcccctc gggaaaaggc cgtggcgata attgagaatt   2220
gcgtccaccc ggattacaag gatatgctca tggagtactt cgaggaggct tgtaagtcct   2280
caggtggcaa caccccacac aaccttgaaa aagccctatc ctggcacact aagttcataa   2340
aaactggctc gatgaagtaa ttagaggaga cacaacatgg agattaaaga gatggtcagt   2400
cttgcgcgca aagctcagaa ggagtatcag gccacccata accaagaagc tgtggacaac   2460
atctgccgag ctgcagcgaa ggttatttac gaaaatgcag caattctggc ccgcgaggca   2520
gtggacgaaa ccggcatggg tgtttacgag cacaaggtgg ccaagaatca aggcaagtcc   2580
aaaggtgttt ggtacaacct gcataacaag aagtcgattg gcatcctcaa tatcgatgag   2640
cgtaccggca tgatcgagat cgcaaaacct atcggggttg taggcgccgt tacgccaacc   2700
accaacccta tcgttactcc gatgagcaac atcatctttg ctcttaagac ctgcaacgcc   2760
atcattatcg ccccacaccc cgcgctccaa aagtgctctg cccacgcagt tcggctgatc   2820
aaagaggcta tcgctccgtt caacgtgccc gaaggtatgg ttcagatcat cgaggagcct   2880
agcatcgaga agacgcagga attgatgggc gccgtagacg tggtcgttgc taccgggggc   2940
atgggcatgg tcaagtctgc ctactcctca gggaagcctt ctttcggtgt cggagccggc   3000
aatgttcagg tgatagtgga cagcaacatc gatttcgaag cggctgcaga aaagatcatc   3060
```

```
accggacgtg ccttcgacaa cggtatcatc tgctcaggcg aacagtccat catctacaac    3120
gaggctgaca aggaagcagt tttcacagca ttccgcaacc acgtgcgta cttttgcgac    3180 gaggccgagg gagatcgggc tcgtgcagcg atcttcgaaa atggagccat cgcgaaagat    3240
gttgtgggcc agtccgttgc ctttattgcc aagaaggcga acattaatat ccccgagggt    3300
actcgtattc tcgtggtcga agctcgcgga gtaggcgccg aagatgtcat ctgtaaagaa    3360
aagatgtgtc cagtcatgtg cgccctctcc tacaagcact cgaagagggg ggtagagatc    3420
gcaaggacga acctcgcaaa cgaaggcaat ggccatacct gtgctatcca ctccaacaac    3480
caagcacaca tcatcttggc aggctcggag ctgaccgtgt ctcgcatcgt ggtcaacgcg    3540
ccaagtgcta ccacagcagg cggtcacatc cagaacggtc ttgccgtcac caatactcta    3600
ggctgcggct cttggggtaa caactcgatc tccgaaaact tcacttataa acacctgctc    3660
aacatttcac gcatcgcccc gttgaactcc agcattcata tcccagatga taaggaaatc    3720
tgggaactct aattagagga gacacaacat gcagcttttc aagctcaaga gcgtcacaca    3780
tcactttgat acttttgcag agtttgccaa ggaattctgt ctcggtgaac gcgacttggt    3840
aattaccaac gagttcatct acgaaccgta tatgaaggca tgccagctgc cttgtcattt    3900
tgtgatgcag agaaatacg gccaaggcga gccttctgac gagatgatga acaacatcct    3960
agcagatatc cgtaatatcc agttcgaccg cgtgatcggg atcggaggtg gtacggttat    4020
tgacatctca aaactctttg ttctgaaggg attaaatgat gttctcgacg cgttcgatcg    4080
caagattccc cttatcaaag agaaagaact gatcattgtg cccaccacct gcggaaccgg    4140
ctcggaggtg acgaacattt ccatcgccga gatcaagtcc cggcacacca agatgggttt    4200
ggctgacgat gcaattgttg ctgaccacgc cataatcatc cctgaacttc tgaagagctt    4260
gcccttccac ttctatgcat gctccgcaat cgatgctctt attcatgcca tcgagtcata    4320
cgtttctcca aaagcgtctc catactcccg tctgttcagt gaggcggcgt gggacattat    4380
cctggaagtt ttcaagaaaa tcgccgaaca cggcccagag taccgcttcg agaagctggg    4440
ggaaatgatc atggccagca actatgccgg tatcgctttc ggcaacgcag gcgttggcgc    4500
cgtccacgct ctatcctacc cgttgggcgg caactatcac gtgccgcatg gagaagcaaa    4560
ctatcagttc ttcaccgagg tctttaaagt ataccaaaag aagaatccgt tcggctatat    4620
tgtcgaactc aactggaagc tctccaagat tctgaactgc cagccagagt acgtgtaccc    4680
gaagctggat gaactgctcg gttgccttct taccaagaaa cctttgcacg aatacggcat    4740
gaaggacgaa gaggttcgtg gcttcgcgga atcggtcctg aagacccagc aacgcttgct    4800
cgccaacaac tacgtcgaac ttactgtcga tgagatcgaa ggtatctacc gacgtctcta    4860
ctaattagag gagacacaac atgaaggatg tactggcgga atacgcctcc cgcattgttt    4920
cggcggagga ggccgttaag cacatcaaaa acggtgaacg ggtagctttg tcacacgctg    4980
ccggcgtgcc tcagagttgc gttgacgcac tggtgcagca ggccgacctt ttccagaatg    5040
tggaaatcta tcacatgctg tgcctcggtg agggtaagta tatggcgcct gagatggccc    5100
ctcacttccg ccacatcacc aactttgtcg gtggtaactc ccgtaaggcg gtcgaagaaa    5160
accgggccga tttcattccg gtattctttt acgaggtgcc aagcatgatt cgcaaagaca    5220
tcctccacat tgatgtcgcc atcgttcagc tttcaatgcc tgacgaaaat ggttactgtt    5280
cctttggagt atcttgcgat tactccaagc cggcagcaga gagcgctcac ctggttatcg    5340
gagaaatcaa ccgtcaaatg ccatacgtac acggcgacaa cttgattcat atctccaagt    5400
```

```
tggattacat cgtgatggca gactacccca tctactctct tgcaaagccc aagatcgggg      5460
aagtcgagga agctatcggg aggaattgtg ccgagcttat tgaagatggt gccactctcc      5520
agctgggaat cggcgcgatt cctgatgcgg ccctgttatt tctcaaggac aaaaaggatc      5580
tgggcatcca taccgaaatg ttctccgatg gtgttgtcga attggttcgc tccggcgtta      5640
tcacaggcaa gaaaaagact cttcacccccg aaagatggt cgcaaccttc ctgatgggaa      5700
gcgaggacgt gtatcatttc atcgataaaa accccgatgt agaactgtat ccagtagatt      5760
acgtgaatga cccgcgtgtg atcgcccaaa acgacaatat ggtctcgatt aacagctgca      5820
tcgaaatcga ccttatggga caggtcgtgt ccgagtgcat cggctcaaag caattcagcg      5880
gcaccggcgg ccaagttgac tacgtgcgtg gcgcagcatg gtctaaaaac ggcaaatcga      5940
tcatggcaat cccgtccact gcaaaaaacg gtacggcatc tcgaattgta cctatcatcg      6000
cggagggcgc tgctgtcacc accctgcgca acgaggtcga ttacgttgta accgagtacg      6060
gtatcgctca gctcaagggc aagagcctgc gccagcgcgc agaggctttg atcgcgatag      6120 cccacccga cttccgtgag gaactaacga acatctccg caagcgattc ggataacata      6180
tggcggccgc aagcttgcct cgacgaaggc gtcaccgtgg gccccctggt tgaggaaaaa      6240
gcacgagaca gcgttgcatc gcttgtcgac gccgccgtcg ccgaaggtgc caccgtcctc      6300
accggcggca aggccggcac aggtgcaggc tacttctacg aaccaacggt gctcacggga      6360
gtttcaacag atgcggctat cctgaacgaa gagatcttcg gtcccgtcgc accgatcgtc      6420
accttccaaa ccgaggaaga agccctgcgt ctagccaact ccaccgaata cggactggcc      6480
tcctatgtgt tcacccagga cacctcacgt atttttccgcg tctccgatgg tctcgagttc      6540
ggcctagtgg gcgtcaattc cggtgtcatc tctaacgctg ctgcacctttt tggtggcgta      6600 aaacaatccg gaatgggccg cgaaggtggt ctcgaaggaa tcgaggagta cacctccgtg      6660
cagtacatcg gtatccggga tccttacgcc ggctaggcta gc                        6702
```

<210> SEQ ID NO 24
<211> LENGTH: 36
<212> TYPE: DNA
<213> ORGANISM: Artificial Sequence
<220> FEATURE:
<223> OTHER INFORMATION: Synthetic 0049-1 for

<400> SEQUENCE: 24

```
gcaggcatgc aagcttaaag tccccacggg tctact                                36
```

<210> SEQ ID NO 25
<211> LENGTH: 36
<212> TYPE: DNA
<213> ORGANISM: Artificial Sequence
<220> FEATURE:
<223> OTHER INFORMATION: Synthetic 0049-2 rev

<400> SEQUENCE: 25

```
ggccagtgcc aagctttacc gatgtactgc acggag                                36
```

<210> SEQ ID NO 26
<211> LENGTH: 3608
<212> TYPE: DNA
<213> ORGANISM: Artificial Sequence
<220> FEATURE:
<223> OTHER INFORMATION: Synthetic adhE2_nt

<400> SEQUENCE: 26

```
aagcttgcat gcctgcaggt cgactctaga ggatccccgg gaggcaccatc acaggtgcaa     60
```

-continued

```
ttattacaca accccacagc gatgtccgca tcctttgatg accccaacct catctcgctt      120
gctggactgg ttccaaccat gcacttagcc gatgctgcca gcctgtccac cttggcccag      180
gaccggttga gcatcaccgg tgataaaggt gccaatgctg gtgcgaagat cgcctcccta      240
gtcgcgggca tggtcgccgg tgctgattcc atcgatgaca tggatgtact ccgccacgga      300
ggtatgcgcc gacttttcga ccggatctac gccccatcca cattgggtc ttttctgcgg       360 gccttcactt tcggccacgt acgccaactc gatgattttg catctgctgc gaaatctttg      420
tttccccgct aaagttgagg acaggttgac acggagttga ctcgacgaat tatccaatgt      480
gagtaggttt ggtgcgtgag ttggaaaaat tcgccatact cgcccttggg ttctgtcagc      540
tcaagaattc ttgagtgacc gatgctctga ttgacctaac tgcttgacac attgcatttc      600
ctacaatctt tagaggagac acaacatgaa agtaaccaat cagaaagagt tgaagcagaa      660
gttgaacgag ctgcgagagg ctcagaagaa gttcgcaacc tacacccagg aacaggtgga      720
caagatcttt aagcagtgtg ccattgcagc cgcgaaagaa cgtattaatc tcgcgaaact      780
tgcggtcgag gaaaccggta ttgggctggt agaagacaag atcatcaaga accacttcgc      840
cgctgaatac atctcacaaca agtacaaaaa cgaaaagaca tgtggtatca tcgaccacga      900
cgacagcttg ggcatcacca aggtagcgga gccaatcggt atcgtcgcag ctatcgtgcc      960
cactactaac cctacctcca ctgctatttt caagtcactc atctccctga aaacccgcaa      1020
tgctatcttc ttctcacctc acccacgcgc taagaaatca actatcgctg cagctaaact      1080
tatcctggat gcagccgtga aagccggggc tccgaaaaac atcatcggtt ggatcgacga      1140
accttccatt gaactctctc aagacctcat gtccgaggca gacattatcc tggcaaccgg      1200
aggcccatcc atggttaaag cagcttacag ctcaggcaag ccggctatcg gcgttggagc      1260
tggtaacact ccagcaatca tcgacgagtc ggccgatatc gacatggcag tgtcctctat      1320
tatcctgtcc aaaacttatg acaacggcgt tatttgcgcg tccgagcagt ctattctcgt      1380
catgaactct atttacgaga aggtaaagga ggagtttgtg aagcgggggt cgtacattct      1440
gaaccagaac gagatcgcta agatcaaaga gactatgttt aaaaacggag ccatcaacgc      1500
agatatcgta gggaagtccg cgtacatcat tgctaagatg gctggaatcg aagtccctca      1560
aaccacgaaa attctgatcg gcgaggtgca atcggtcgaa aagtccgagc tgttctcgca      1620
tgaaaagttg tccccggtcc tcgcgatgta taaagttaag gattttgatg aagcactcaa      1680
gaaagctcag cgcctgatcg aattgggtgg ctcgggtcac acctcttccc tctacattga      1740
ctcccagaac aataaagata aggtgaaaga gttcggcctg gctatgaaga cgtctcgtac      1800
cttcatcaat atgccctctt cacagggcgc cagcggtgac ctttacaatt tcgctatcgc      1860
tcctagcttt accctcggct gcggcacctg ggcggtaat tctgtgtccc aaaacgtcga      1920
accaaagcat ctgctcaaca ttaaaagcgt cgccgaacgt cgcgagaaca tgttgtggtt      1980
caaggtcccg caaaaatct acttcaagta tggttgcttg cgctttgcac ttaaagagct      2040
taaggacatg aataaaaagc gggcgttcat cgtcactgat aaggatctgt tcaaactggg      2100
ctatgttaac aagattacca aggtcctgga tgagatcgat atcaagtatt ccatcttcac      2160
cgatattaag tccgatccga ccattgattc cgtgaagaag ggcgcgaagg agatgctcaa      2220
ctttgaaccc gacacgatta tttctattgg cggaggcagc ccaatggacg cagctaaggt      2280
tatgcacctg ctgtatgagt acccagaagc agagatcgag aaccttgcaa tcaatttcat      2340
ggatattcgc aaacgcattt gcaactttcc taagcttggt acaaaagcta tctctgttgc      2400
```

```
gatccctacc accgcaggaa ccggcagcga agcgacacca ttcgccgtta ttaccaacga    2460
tgaaacaggt atgaagtacc cacttacctc ttatgaactt accccgaaca tggctatcat    2520
tgatacggaa ttgatgctga acatgccgcg gaagttgacc gcagctacgg gaatcgatgc    2580
attggttcat gcaatcgagg catacgtttc cgtcatggca accgattaca ccgacgagct    2640
cgcgttgcgt gcgattaaaa tgatcttcaa gtaccttcca cgcgcataca agaatggcac    2700
aaacgatatt gaagcccgag aaaagatggc acacgcttcg aacatcgctg gtatggcctt    2760
cgcgaatgcg tttctcggag tgtgtcactc catggcgcac aaactgggag ccatgcatca    2820
cgtgccccac ggtatcgcat gcgccgttct tattgaagag gtgatcaagt ataatgccac    2880
cgattgcccc actaagcaga cggccttccc tcagtacaaa tcgcccaatg ccaagcgtaa    2940
atacgcggaa attgccgagt acttgaacct taagggacc agcgacacgg aaaaggtgac    3000
cgcactgatt gaagccatct ccaagcttaa gatcgacctg agcatcccac aaaacatctc    3060
agcagccggc attaacaaga aggacttcta caacactctc gacaagatgt cagagctcgc    3120
cttcgatgat cagtgcacta ccgcaaaccc acgttatccg ctcatctctg aactgaagga    3180
tatctacatc aagtcgtttt aatttgatca cggccattca ccaccgtaac cggtagctcc    3240
ctgaccaccc agccgagctt tcggcgtgag atgacaacaa ttcgtggaac aaccagaaca    3300
agacgtgatc tggcgatcac ccctacccga aaattccgga cccgcccgga accgggatca    3360
ggacatcacc gagggcacat cggtggatcg aggcttaatg gaacgcccca ctcatccaat    3420
ccggcaattt tgatgctgta cccatcgacg catggtgctc caaatacgtg gaagccatca    3480
cggtcacgga tgaagcatgg caggttttcc ggttggaagt ccactggatt gttgggcagg    3540
aaccaggtga gcgcctgaat ggcgaatggc gataagctag aggatccccg ggtaccgagc    3600
tcgaattc                                                             3608

<210> SEQ ID NO 27
<211> LENGTH: 20
<212> TYPE: DNA
<213> ORGANISM: Artificial Sequence
<220> FEATURE:
<223> OTHER INFORMATION: Synthetic AdhE2_1_F

<400> SEQUENCE: 27
atgaaagtaa ccaatcagaa                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic AdhE2_2260_R

<400> SEQUENCE: 28
aatcggtggc attatacttg                                                  20
```

METHOD OF SCREENING GENE FOR 1,4-BDO PRODUCTION

CROSS-REFERENCE TO RELATED APPLICATIONS

This application claims the benefit of Korean Patent Application No. 10-2013-0100567, filed on Aug. 23, 2013, in the Korean Intellectual Property Office, the disclosure of which is incorporated herein in its entirety by reference.

BACKGROUND

1. Field

One aspect relates to a method of screening a protein involved in efficiently producing 1,4-BDO. Another aspect relates to a microorganism the nucleic acid encoding the protein screened by the method. Another aspect also relates to a method of producing 1,4-BDO at a high efficiency using the microorganism.

2. Description of the Related Art 1,4-butandiol (1,4-BDO) is used not only as a solvent for manufacturing plastics and fiber but also as a raw material for producing fiber such as spandex. About 1.3 million tons of 1,4-BDO is produced in a year worldwide from petroleum-based materials such as acetylene, butane, propylene, and butadiene. In addition, about 6% of consumption increase is anticipated each year. 1,4-butandiol is important as it is used throughout the entire chemical industry for the production of various chemicals such as polymers, solvents, and fine chemistry intermediates. Most of the chemicals having a carbon number of four are currently synthesized by being derived from 1,4-butandiol or maleic anhydride, but the chemical production process needs to be improved or replaced by a newly developed process as production costs are increasing due to rising oil prices. Thus, biological processes using microorganisms are suggested as the alternative processes.

Different from the method of producing 1,4-BDO chemically, Genomatica Inc. established in 2011 a biosynthetic pathway of producing 1,4-BDO using succinyl-CoA synthetase (Cat1), succinate semialdehyde dehydrogenase (SucCD), NAD-dependent 4-hydroxybutyrate dehydrogenase (4Hbd), 4-hydroxybutyryl CoA:acetyl-CoA transferase (Cat2), and alcohol dehydrogenase (AdhE2) genes in an *Escherichia coli*. However, there has been an attempt to establish a new biosynthetic pathway by altering the biological pathways which have already been shown in an *Escherichia coli* in order to produce 1,4-BDO more efficiently. The attempt is much focused on discovering enzymes of high efficiency by inducing various genetic mutations in enzyme genes.

However, such an approach alone is limited in effectively discovering a protein or a gene related to producing of 1,4-BDO. A novel approach was tried to solve the problem, and the genes screened by the approach were verified to enable a significant increase of 1,4-BDO production.

SUMMARY

An aspect provides a screening method of a protein involved in efficient production of 1,4-BDO. Another aspect provides a microorganism including a nucleic acid encoding a protein screened in the method. Another aspect provides a method of producing 1,4-BDO at a high efficiency using the microorganism.

BRIEF DESCRIPTION OF THE DRAWINGS

These and/or other aspects will become apparent and more readily appreciated from the following description of the embodiments, taken in conjunction with the accompanying drawings of which:

FIG. 1 compares growth curves of a wild type CGL strain and a CGL strain capable of producing 1,4-BDO in the cases where wild type CGL strain and the CGL strain capable of producing 1,4-BDO were treated with 1,4-BDO of different concentrations. WT+BDO 25, 50, and 100 denote that 1,4-BDO was added to the wild type CGL at the concentrations of 25 g/L, 50 g/L, and 100 g/L, respectively. adhE2+BDO 25, 50, and 100 denote that 1,4-BDO was added to the CGL transformed to produce 1,4-BDO at the concentrations of 25 g/L, 50 g/L, and 100 g/L, respectively;

FIG. 2 shows the result of 2D-gel electrophoresis was obtained from proteins produced in the CGL strain cultured in a LB culture medium at 30° C.;

FIGS. 3a and 3b respectively show the result of 2D-gel electrophoresis of proteins produced in the wild type CGL and the mutant strain CGL (Δldh 4G adhE2) after each of the CGL strain was cultured in a LB culture medium at 30° C.;

FIG. 4(A) to (G) shows 2D-gel electrophoresis spots of CGL strain wherein intensity was increased. The left shows proteins which were expressed when the wild type CGL was treated with 1,4-BDO of a concentration of 100 g/L. The right shows proteins which were expressed when the mutant strain CGL (Δldh 4G adhE2) producing 1,4-BDO was treated with 1,4-BDO of a concentration of 100 g/L; and FIG. 5 compares the 1,4-BDO productivity of CGL wherein an identified gene is over-expressed. pEKEx1 denotes a null vector as a control group. pEk0827 denotes a vector expressing NCgl0827. pEk2145 denotes a vector expressing NCgl2145. pEk0630 denotes a vector expressing NCgl0630. pEk2826 denotes a vector expressing NCgl2826.

DETAILED DESCRIPTION

An aspect of the present invention provides a method of screening a protein involved in efficient production of 1,4-BDO.

An embodiment of the present invention provides a method of screening a protein positively involved in 1,4-BDO production, including culturing a microorganism producing 1,4-BDO in a culture medium either including 1,4-BDO or not including 1,4-BDO; screening a protein showing an increased expression according to increase of 1,4-BDO concentration from culture solution; and selecting the screened protein as a protein positively involved in 1,4-BDO production.

The protein screening method is described in detail below.

First, the protein screening method includes culturing a microorganism producing 1,4-BDO in a culture medium either including 1,4-BDO or not including 1,4-BDO. The microorganism, which is a microorganism producing 1,4-BDO, may be a wild type microorganism or a transformed mutant microorganism. The microorganism may be a microorganism capable of producing 1,4-BDO. The microorganism may be a wild type microorganism capable of producing 1,4-BDO. Also, the microorganism may be a microorganism where introduction of genes associated with 1,4-BDO biosynthesis makes the microorganism be capable of producing 1,4-BDO. The microorganism may be a microorganism of a *Corynebacterium* genus. The microorganism of *Corynebacterium* genus may be an *Corynebacterium glutamicum*.

The microorganism capable of producing 1,4-BDO may include an enzyme converting succinyl CoA to succinyl semialdehyde, an enzyme converting succinyl semialdehyde to 4-hydroxybutyrate, an enzyme converting 4-hydroxybutyrate to 4-hydroxybutyrate-CoA, an enzyme converting 4-hydroxybutyrate-CoA to 1,4-BDO, or the combination thereof.

The enzyme converting succinyl CoA to succinyl semialdehyde may be CoA-dependent succinate semialdehyde dehydrogenase. The enzyme may be an enzyme classified as EC.1.2.1.76. An example of the enzyme may be SucD. The enzyme converting succinyl semialdehyde to 4-hydroxybutyrate may be 4-hydroxybutyrate dehydrogenase. The enzyme may be an enzyme classified as EC.1.1.1.61. The enzyme may be 4Hbd. In addition, the enzyme converting 4-hydroxybutyrate to 4-hydroxybutyrate-CoA may be 4-hydroxybutyryl CoA:acetyl-CoA transferase. The enzyme may be an enzyme classified as EC.2.8.3.-. An example of the enzyme may be Cat2. The enzyme converting 4-hydroxybutyrate-CoA to 1,4-BDO may be alcohol dehydrogenase. The alcohol dehydrogenase may be an enzyme classified as EC.1.1.1.-. The enzyme may be AdhE or AdhE2. As an example, the microorganism producing 1,4-BDO may be an microorganism expressing the SucD protein, the 4Hbd protein, the Cat2 protein, and the AdhE protein.

The term "protein expression" herein means that a protein or an enzyme exists and has activity in a microorganism. The protein or enzyme may exist through a transcription and a translation where a polynucleotide encoding the protein, existing in the microorganism, is transcribed to an mRNA which is in turn translated into the protein. The polynucleotide encoding the protein may exist either by being inserted in a chromosome of a microorganism or by being inserted in a plasmid vector.

The CoA-dependent succinate semialdehyde dehydrogenase may be a protein derived from an *Escherichia* genus, a *Corynebacterium* genus or a *Porphyromonas* genus. The SucD protein may have an amino acid sequence of SEQ ID NO:10. The polynucleotide encoding the SucD may have a nucleotide sequence of SEQ ID NO:15.

The 4-hydroxybutyrate dehydrogenase may be a protein derived from an *Escherichia* genus, a *Corynebacterium* genus or a *Porphyromonas* genus. The 4Hbd protein may have an amino acid sequence of SEQ ID NO:7. The polynucleotide encoding the 4HbD may have a nucleotide sequence of SEQ ID NO:12.

The 4-hydroxybutyryl CoA:acetyl-CoA transferase may be a protein derived from an *Escherichia* genus, a *Corynebacterium* genus or a *Porphyromonas* genus. The Cat2 protein may have an amino acid sequence of SEQ ID NO:8. The polynucleotide encoding the Cat2 may have a nucleotide sequence of SEQ ID NO:13.

The alcohol dehydrogenase may be a protein derived from *Clostridium acetobutylicum*. The AdhE protein may have an amino acid sequence of SEQ ID NO:9. The polynucleotide encoding the AdhE may have a nucleotide sequence of SEQ ID NO:14.

The microorganism may additionally include succinyl CoA:coenzyme A transferase. The succinyl CoA:coenzyme A transferase may have an activity to catalyze a reaction converting succinate to succinyl CoA. The enzyme may be an enzyme classified as EC.2.8.3.-. As an example, the enzyme may be Cat1. The Cat1 may have an amino acid sequence of SEQ ID NO:11. The polynucleotide encoding the Cat1 may have a nucleotide sequence of SEQ ID NO:16.

The microorganism may be a microorganism wherein a pathway synthesizing lactate from pyruvate is inactivated or decreased. The microorganism may have the eliminated or decreased activity of lactate dehydrogenase (Ldh). The Ldh may have an activity catalyzing a reaction converting pyruvate to lactate. The Ldh may be an enzyme classified as EC.1.1.1.27. The microorganism may have the inactivated or attenuated gene encoding lactate dehydrogenase.

The term "inactivation" herein may mean that a gene which is not expressed or which is expressed but produces the enzyme or the protein without activity, is produced. The term "attenuation" may mean that a gene of which expression is decreased to a level lower than an expression level of wild type strain, a strain which is not genetically engineered or a parent strain or a gene which is expressed but produces the enzyme or the protein with a decreased activity, is produced. A decreased Ldh activity in the microorganism may be lower than 30%, 20% or 10% of the Ldh activity of wild type microorganism. The Ldh activity in the microorganism may be completely eliminated. The inactivation or the attenuation may be caused by homologous recombination. The inactivation or attenuation may be performed by introducing a vector including a part of the sequence of the genes into a cell, culturing the cell so that homologous recombination between the sequence and an endogenous gene of the cell may occur, and then selecting a cell wherein homologous recombination has occurred using a selection marker. The microorganism may be a microorganism wherein activity of an enzyme encoded by the gene may be eliminated or decreased by inactivation or attenuation of the gene. The term "decrease" may relatively represent the activity of the genetically engineered microorganism in comparison to the activity of a microorganism which is not genetically engineered.

Activity of the lactate dehydrogenase may be inactivated or attenuated in the microorganism by a mutation of gene encoding the lactate dehydrogenase. The mutation may be performed by substitution, partial or total deletion, or addition of a nucleotide. Activity of the lactate dehydrogenase in the microorganism may be decreased by eliminating endogenous lactate dehydrogenase gene. The elimination includes not only physical elimination of the gene but also prevention of functional expression of the gene. The elimination may be performed by homologous recombination.

The term "transformation" herein refers to introducing a gene to a microorganism so that the gene may be expressed in the microorganism. The introduced gene, if the gene is expressed in the microorganism, may be inserted into a chromosome of the microorganism or exists outside a chromosome. The gene may be a polynucleotide capable of encoding a polypeptide, which may be DNA or RNA. The introduction of the gene may be any type of introduction, only if the gene may be introduced into and expressed in the microorganism. For example, the gene may be introduced into a microorganism in the form of an expression cassette, a polynucleotide construct including all elements necessary to be expressed by itself. The expression cassette usually includes a promoter, a transcription termination signal, a ribosome binding site, and a translation termination signal operably linked with the gene. The expression cassette may be an expression vector capable of self-replication. The gene may be introduced as itself or in the form of a polynucleotide construct to a host cell and be operably linked with a sequence required for an expression in the microorganism.

The term "sequence identity" of a nucleic acid or a polypeptide herein means the degree of identity with reference to base-to-base or amino acid-to-amino acid comparison or with reference to function or structure in a whole window of comparison. Therefore, "percentage of sequence identity" may be calculated, for example, by comparing two optimally aligned sequences in a whole window of comparison, determining the number of positions wherein the same base or the same amino acid is located in both sequences and obtaining the number of matched positions, and by dividing the number of the matched positions with the total number of positions (i.e., window size) and then multiplying 100 with the resulting value. The percent sequence identity may be determined by using known sequence comparing software such as BLASTn (NCBI) and MEGALIGN™ (DNASTAR Inc). Various levels of sequence identity may be used to identify many polypeptides or genes having an identical or similar function or activity. For example, a percent sequence identity of 50%, 55%, 60%, 65%, 70%, 75%, 80%, 85%, 90% or 95% may be used.

1,4-BDO may be added to culture medium in any phase in the growth curve of a microorganism. 1,4-BDO may be added to culture medium in exponential phase wherein a microorganism grows most actively. In addition, concentration of the added 1,4-BDO may be from about 0 to about 500 g/L. For example, the concentration of the added 1,4-BDO may be selected from the range from about 0 to about 400 g/L, from about 0 to about 300 g/L, from about 0 to about 200 g/L, or from about 0 to about 100 g/L. Two or n different concentrations of 1,4-BDO may be treated (n is a integer equal to or greater than 2.). When 1,4-BDO is added, at least two different concentrations, for example, three or more, four or more, or five or more different concentrations of 1,4-BDO may be added to culture medium.

Microorganism culture conditions may be dependent on the microorganism. The term "culture conditions" refers to conditions to culture a microorganism. The culture condition may be, for example, carbon source, nitrogen source or oxygen conditions. Carbon sources which may be used by a microorganism include monosaccharide, disaccharide or polysaccharide. Specifically, glucose, fructose, mannose, or galactose etc. may be used. Nitrogen sources which may be used by a microorganism include organic nitrogen compounds and inorganic nitrogen compounds. Specifically, amino acids, amides, amines, nitrates or ammonium salts etc. may be used.

The protein screening method also includes screening a protein showing an increased expression according to increase of 1,4-BDO concentration from culture solution. A protein produced by a microorganism refers to all proteins produced by a microorganism, and may be proteins existing in or secreted by a microorganism.

The protein screening method may additionally include a step of collecting cultured microorganism and a step of extracting a protein from the microorganism in order to compare the protein quantity. Methods including SDS-PAGE or Western blot may be used to compare the protein quantity. In addition, the protein quantity may be verified through two-dimensional gel electrophoresis or matrix-assisted laser desorption ionization-time of flight mass spectrometry (MALDI-TOF/MS).

A protein expressed to a higher level at a higher 1,4-BDO concentration may be screened in the steps. After treating with 1,4-BDO of two different concentrations, a protein expressed to a higher level under a higher 1,4-BDO concentration may be screened. In addition, when 1,4-BDO of two or n different concentrations is treated, a protein commonly expressed to a higher level in comparison to an expression level at the lowest 1,4-BDO concentration may be screened (n is a integer equal to or greater than 2.). In addition, a protein of which expression level is increased as the 1,4-BDO concentration is increased may be screened.

The protein screening method also includes selecting the screened protein as a protein positively involved in 1,4-BDO production. The selected protein in the above steps may be a protein involved in 1,4-BDO production. The protein may be directly or indirectly involved in 1,4-BDO production by a microorganism. The protein with an increased expression may be expressed in a cell.

The culturing may include culturing a wild type microorganism incapable of producing 1,4-BDO and a mutant microorganism thereof capable of producing 1,4-BDO. The screening may additionally include screening of a protein of which expression is higher in the mutant microorganism capable of producing 1,4-BDO than that in the wild type microorganism incapable of producing 1,4-BDO.

The method may include culturing a wild type microorganism incapable of producing 1,4-BDO and a mutant thereof capable of producing 1,4-BDO, analyzing a protein produced by the microorganisms, and screening a protein of which expression is higher in a mutant capable of producing 1,4-BDO than that in a wild type microorganism.

A wild type microorganism incapable of producing 1,4-BDO and a mutant microorganism capable of producing 1,4-BDO may be the same type as the microorganism producing 1,4-BDO used in the method. In addition, the wild type microorganism refers to a microorganism which is not yet mutated to produce 1,4-BDO. The culture conditions may be the same as the culture conditions used in the screening method. A wild type microorganism and a mutant thereof capable of producing 1,4-BDO may be cultured at the same 1,4-BDO concentration or in the absence of 1,4-BDO. The protein of which expression is increased may be expressed in a cell.

The protein screening method also includes comparing proteins expressed at a high level in the culturing and selecting a protein commonly expressed in the screening.

When 1,4-BDO of different concentrations is added, a protein expressed at a higher level in a microorganism to which 1,4-BDO of a higher concentration is added may be screened. In addition, a protein expressed at a higher level in a microorganism to which 1,4-BDO is added than that in a microorganism to which 1,4-BDO is not added may be screened. When 1,4-BDO of a higher concentration is added, a protein expressed at a higher level may be screened. In addition, a protein commonly expressed in all microorganisms to which 1,4-BDO of different concentrations is added may be screened. In addition, a protein of which expression level is increased as 1,4-BDO is increased may be screened.

An over-expressed protein may be verified by the screening. For example, the protein may be citrate synthase NCgl0630 or NCgl2145. Production of 1,4-BDO may be increased by introducing a nucleic acid sequence encoding an over-expressed protein such as NCgl0630 or NCgl2145 into a microorganism capable of producing 1,4-BDO. In an Example of the present invention, 1,4-BDO productivity of a strain wherein NCgl0630 was introduced was 49% higher than that of the control group. In addition, 1,4-BDO productivity of a strain wherein NCgl2145 was introduced was 18% higher than that of the control group. These results verified that the a protein involved in 1,4-BDO production may be effectively screened by the screening method.

An aspect relates to a microorganism including a nucleic acid encoding a protein screened by the method. An Example of the present invention provides a microorganism, which is capable of producing 1,4-BDO, wherein activity of citrate synthase is increased. The activity of citrate synthase may be increased in comparison with that of a wild type of the microorganism. In addition, the microorganism is capable of producing 1,4-BDO at a high level.

The microorganism, which is a microorganism producing 1,4-BDO, may be a wild type microorganism or a transformed microorganism. The transformed microorganism may be prepared by an addition, deletion, or substitution of a gene to produce 1,4-BDO in a wild type microorganism. In addition, the transformation may be performed by mutating one or more genes. The microorganism may be *Corynebacterium glutamicum* (CGL). Activity of Ldh in a wild type CGL may be eliminated for producing 1,4-BDO. In addition, cat1, sucD, 4hbD, cat2, and adhE genes may be introduced into a wild type CGL for producing 1,4-BDO.

The citrate synthase may be a gene derived from a CGL. In amino acids constituting the citrate synthase, part of the amino acid may be substituted, altered or deleted, as long as the sequence retains original activity of citrate synthase. In addition, the citrate synthase may include an amino acid sequence having at least 95% of sequence identity with an amino acid sequence of SEQ ID NO:1. For example, the citrate synthase may include an amino acid sequence of SEQ ID NO:1.

A nucleic acid sequence encoding the citrate synthase may include a nucleic acid sequence encoding an amino acid sequence having at least 95% of sequence identity with an amino acid sequence of SEQ ID NO:1. For example, the nucleic acid may have a nucleic acid sequence of SEQ ID NO:2. Part of the nucleic acid sequence may be substituted, altered, or deleted, as long as the protein encoded by the nucleic acid sequence retains original activity of citrate synthase. The nucleic acid may be a nucleic acid sequence having 80% or higher, 90% or higher, or 95% or higher sequence identity with the nucleic acid sequence, as long as the protein encoded by the nucleic acid sequence retains original activity of citrate synthase.

Activity of citrate synthase may be increased by over-expressing a nucleic acid encoding citrate synthase in a cell. The nucleic acid may be introduced to a microorganism as itself or as it is inserted to a vector. The nucleic acid may be expressed within a vector or over-expressed as it is inserted into a chromosome of a microorganism.

The term "vector" herein refers to a DNA product including a DNA sequence operably linked to an appropriate regulatory sequence capable of expressing DNA in an appropriate host. The vector may be a plasmid vector, a bacteriophage vector, or a cosmid vector.

To operate as an expression vector, a vector may include a replication origin, a promoter, a multi-cloning site (MCS), and a selection marker. A replication origin gives a function to a plasmid to replicate itself independently of host cell chromosome. A promoter operates in transcription process of an inserted foreign gene. An MCS enables a foreign gene to be inserted through various restriction enzyme sites. A selection marker verifies whether a vector has been properly introduced to a host cell or not. A selection includes an antibiotic-resistant gene generally used in the art. For example, a selection marker may include a gene resistant to ampicillin, gentamycin, carbenicillin, chloramphenicol, streptomycin, kanamycin, geneticin, neomycin, or tetracycline. Considering the cost, ampicillin or gentamycin-resistant gene may be used.

When a vector of an aspect of the present invention uses a prokaryotic cell as host cell, a strong promoter, for example, lamda-PL promoter, trp promoter, lac promoter, T7 promoter, or tac promoter is included in the vector. If a vector uses a eukaryotic cell as host cell, the vector may include a promoter derived from genome of a mammal (metallothionin promoter, e.g.) or a promoter derived from a mammal virus (adenovirus late promoter, vaccinia virus 7.5K promoter, SV40 promoter, cytomegalovirus promoter or tk promoter of HSV promoter, e.g.). The promoter may be a lamda-PL promoter, trp promoter, lac promoter, T7 promoter, or tac promoter. In this manner, a promoter is operably linked with a sequence encoding a gene.

The term "operably linked" herein may mean a functional linkage between a nucleic acid expression regulatory sequence (promoter, signal sequence, or a sequence at transcription regulation factor binding site) and another nucleic acid sequence. Through the functional linkage, the regulatory sequence may control transcription and/or translation of a nucleic acid encoding the gene.

A microorganism in another Example of the present invention may include NCgl2145 protein which is not included in a wild type microorganism. The microorganism provides a microorganism, which is capable of producing 1,4-BDO, including NCgl2145 protein. NCgl2145 protein may include an amino acid sequence having at least 95% of sequence identity with an amino acid sequence of SEQ ID NO:3. For example, NCgl2145 protein may include an amino acid sequence of SEQ ID NO:3.

A nucleic acid sequence encoding the NCgl2145 protein may include a nucleic acid sequence encoding an amino acid sequence having at least 95% of sequence identity with an amino acid sequence of SEQ ID NO:3. For example, the nucleic acid encoding the NCgl2145 protein may have a nucleic acid sequence of SEQ ID NO:4. The nucleic acid encoding amino acid sequence of SEQ ID NO:3 may be a nucleic acid sequence having 80% or higher, 85% or higher, 90% or higher, 95% or higher, or 99% or higher sequence identity with a nucleic acid sequence of SEQ ID NO:4 or a fragment thereof. For example, the amino acid sequence of SEQ ID NO:3 may be encoded by the sequence of SEQ ID NO:4. In addition, the microorganism provides a microorganism, which is capable of producing 1,4-BDO, wherein a nucleic acid sequence encoding an amino acid sequence having at least 95% of sequence identity with an amino acid sequence of SEQ ID NO:3 is introduced. The microorganism may additionally include a nucleic acid encoding an amino acid sequence having at least 95% of sequence identity with an amino acid sequence of SEQ ID NO:3, in comparison with a wild type microorganism. The microorganism is capable of producing 1,4-BDO at a high level.

The microorganism may be CGL. Ldh activity may be eliminated in a wild type CGL for producing 1,4-BDO. For example, cat1, sucD, 4hbD, cat2, and adhE genes may be introduced into a wild type CGL for producing 1,4-BDO.

Another example of the present invention provides a microorganism wherein nucleic acids encoding citrate synthase and NCgI2145 (hypothetical protein) are introduced. The microorganism overexpressing the two enzymes at the same time is capable of producing 1,4-BDO at a high level.

The microorganism may be CGL. The citrate synthase may have an amino acid sequence of SEQ ID NO:1. The amino acid sequence of SEQ ID NO:1 may be encoded by a nucleic acid sequence of SEQ ID NO:2. In addition, the citrate synthase may be derived from CGL. The NCgI2145 may have an amino acid sequence of SEQ ID NO:3. In addition, the amino acid sequence of SEQ ID NO:3 may be encoded by a nucleic acid sequence of SEQ ID NO:4. The microorganism may be CGL. Ldh activity may be eliminated in a wild type CGL for producing 1,4-BDO. Nucleic acids encoding Cat1, SucD, 4HbD, Cat2, and AdhE may be introduced into a wild type CGL for producing 1,4-BDO.

Another aspect provides a method of producing a microorganism having an increased capability of producing 1,4-BDO, the method including introduction of a nucleic acid encoding a screened protein positively involved in 1,4-BDO production to a microorganism capable of producing 1,4-BDO.

The protein positively involved in 1,4-BDO production may be citrate synthase or a protein having an amino acid sequence of SEQ ID NO:3. The citrate synthase may have an amino acid sequence of SEQ ID NO:1. The citrate synthase may be encoded by a nucleic acid sequence of SEQ ID NO:2. In addition, the amino acid sequence of SEQ ID NO:3 may be encoded by a nucleic acid sequence of SEQ ID NO:4. The microorganism may be CGL. Ldh activity may be eliminated in a wild type CGL for producing 1,4-BDO. A nucleic acid encoding one protein selected from the group consisting of Cat1, SucD, 4HbD, Cat2, and AdhE may be introduced into a wild type CGL for producing 1,4-BDO. In addition, the microorganism may include Cat1, SucD, 4HbD, Cat2, and AdhE all together.

Another aspect provides a method of producing 1,4-BDO including culturing a microorganism wherein a nucleic acid encoding a protein positively involved in 1,4-BDO production is introduced; and obtaining 1,4-BDO from culture medium.

The microorganism may be CGL. Ldh activity may be eliminated in a wild type CGL for producing 1,4-BDO. sucD, 4hbD, cat2, and adhE genes may be introduced into a wild type CGL for producing 1,4-BDO. In addition, the microorganism may additionally include a nucleic acid encoding Cat1 or nucleic acid encoding SucCD.

To over-expressing in a cell a nucleic acid encoding a protein screened by the screening method, a nucleic acid may be introduced to a microorganism as itself or as it is inserted to a vector. The nucleic acid may be expressed within a vector or over-expressed as it is inserted into a chromosome of a microorganism. A vector for expression may include a replication origin, a promoter, an MCS, and a selection marker.

Another example of the present invention provides a method of producing 1,4-BDO at a high yield including culturing a microorganism wherein citrate synthase is over-expressed, Ncgl 2145 is introduced, or a nucleic acid encoding a screened protein is introduced; and obtaining 1,4-BDO from culture medium.

The culturing may be performed under an appropriate culture medium and culture conditions known in this art. The culture medium and culture conditions may be conveniently adjusted according to the selected microorganism. The culturing method may include batch culturing, continuous culturing, fed-batch culturing or a combination thereof.

The culture medium may include various carbon sources, nitrogen sources, and trace elements.

The carbon source may include a carbohydrate such as glucose, sucrose, lactose, fructose, maltose, starch, and cellulose, a lipid such as soybean oil, sunflower oil, castor oil, and coconut oil, a fatty acid such as palmitic acid, stearic acid, and linoleic acid, an organic acid such as acetic acid or a combination thereof. The culturing may be performed by using glucose as a carbon source. The nitrogen source may include an organic nitrogen source such as peptone, yeast extract, meat extract, malt extract, corn steep liquid, and soybean, an inorganic nitrogen source such as urea, ammonium sulfate, ammonium chloride, ammonium phosphate, ammonium carbonate, and ammonium nitrate or a combination thereof. The culture medium may include as a phosphorous source, for example, potassium dihydrogen phosphate, dipotassium phosphate, a sodium-containing salt corresponding to potassium dihydrogen phosphate, and dipotassium phosphate, and a metal salt such as magnesium sulfate and iron sulfate. The culture medium or an individual component may be added to the culture in a batch mode or a continuous mode. The culture medium or an individual component may be added to the culture solution in a batch mode or a continuous mode.

In addition, pH of the culture may be adjusted during the culturing by adding a compound such as ammonium hydroxide, potassium hydroxide, ammonia, phosphoric acid or sulfuric acid to the culture in an appropriate mode. In addition, bubble formation may be repressed by using an endoplasmic reticulum such as fatty acid polyglycol ester.

The culturing may be performed under anaerobic conditions. The term "anaerobic conditions" herein refers to a state wherein oxygen content is lower than that of normal atmospheric state. Anaerobic conditions may be formed, for example, by supplying carbon dioxide or nitrogen at a flow rate range from about 0.1 vvm (Volume per Volume per Minute) to about 0.4 vvm, from about 0.2 vvm to about 0.3 vvm or at a flow rate of 0.25 vvm. In addition, anaerobic conditions may be formed by setting an aeration rate in the range from about 0 vvm and to 0.4 vvm, from about 0.1 vvm to about 0.3 vvm or from 0.15 vvm to about 0.25 vvm.

The method of producing 1,4-BDO includes recovering of the produced 1,4-BDO from the culture medium. For example, the recovery of 1,4-BDO may be performed by using known separation and purification methods. The recovery may be performed by centrifugation, ion exchange chromatography, filtration, precipitation or a combination thereof.

As described above, according to a screening method of one Example of the present invention, a gene for producing 1,4-BDO at a high efficiency may be effectively screened. In addition, a microorganism over-expressing NCgl0630 gene encoding citrate synthase and NCgl2145 gene screened by the screening method is capable of producing 1,4-BDO effectively. 1,4-BDO may be effectively produced by the method and with the genes.

It should be understood that the exemplary embodiments described therein should be considered in a descriptive sense only and not for purposes of limitation. Descriptions of features or aspects within each embodiment should typically be considered as available for other similar features or aspects in other embodiments.

Example 1. Preparation of *Corynebacterium* Microorganism Wherein Endogenous Lactate Dehydrogenase Gene is Deleted A decrease in intracellular acetyl-CoA concentration was found when culturing *Corynebacterium glutamicum* ATCC13032 under anaerobic conditions. Therefore, it was assumed that decrease in TCA cycle activity may be caused by the decrease in the acetyl-CoA concentration. In addition, an experiment was designed in search of a method to resolve the problem. For this, a Δldh *Corynebacterium* microorganism ATCC13032 wherein endogenous lactate dehydrogenase gene is deleted ("basic strain" hereinafter) was prepared by deleting the endogenous lactate dehydrogenase gene so that the Pdh enzyme activity might be conveniently measured in the natural *Corynebacterium glutamicum*.

1.1 Preparation of Replacement Vector

The L-lactate dehydrogenase gene of *Corynebacterium glutamicum* (CGL) ATCC13032 was inactivated by homologous recombination using a pK19 mobsacB (ATCC87098)

vector. The two homologous regions for the elimination of the ldhA gene were obtained by PCR amplification using the genome DNA of CGL ATCC13032. Two homologous regions for the elimination of the ldh gene were located upstream and downstream from the gene and obtained by PCR amplification using a primer set including ldhA_5'_HindIII (SEQ ID NO:17) and ldhA_up_3'_XhoI (SEQ ID NO:18) and a primer set including ldhA_dn_5'_XhoI (SEQ ID NO:19) and ldhA_3'_EcoRI (SEQ ID NO:20). The PCR amplification was performed by repeating, 30 times, a cycle including a denaturation step at 95° C. for 30 seconds, an annealing step at 55° C. for 30 seconds, and an extension step at 72° C. for 30 seconds. All the PCR amplifications hereinafter were performed under the same conditions. A pK19_ΔldhA vector was prepared by cloning the obtained amplification product to the HindIII and EcoRI restriction enzyme positions of pK19 mobsacB vector.

1.2 Preparation of CGL (ΔldhA) Strain

The pK19_ΔldhA vector was introduced to CGL ATCC13032 by electroporation. The strain wherein the pK19_ΔldhA vector was introduced was cultured at 30° C. by streaking the strain on a lactobacillus selection (LBHIS) culture medium including kanamycin 25 μg/ml. The LBHIS culture medium included brain-heart infusion broth 18.5 g/L, 0.5 M sorbitol, 5 g/L bacto-tryptone, 2.5 g/L bacto-yeast extract, 5 g/L NaCl, and 18 g/L bacto-agar. Hereinafter, the composition of the LBHIS culture medium is the same. Colonies on the culture medium were streaked on an LB-sucrose culture medium and cultured at 30° C., and then only the colonies wherein double crossing-over occurred were selected. After separating genomic DNA from the selected colonies, deletion of the ldhA gene was verified by PCR using a primer set including ldhA up (SEQ ID NO:21) and ldhA down (SEQ ID NO:22). CGL (ΔldhA) strain (B005) was obtained as a result.

Example 2. Introduction of Genes for 1,4-BDO Production 2.1 Preparation of pK19 gapA::4G Vector A CGL strain capable of producing 1,4-BDO was prepared on the basis of the strain prepared above. To insert four genes of cat1, sucD, 4hbD, and cat2 into a chromosome of the strain, pK19 gapA::4G vector for the insertion of cat1, sucD 4hbD, and cat2 genes was prepared on the basis of pK19 mobsacB. The pK19 gapA::4G vector was prepared by synthesizing whole 4G gene having a nucleotide sequence of SEQ ID NO:23 and cloning the 4G gene into the NheI and XbaI restriction enzyme sites of the pK19 mobsacB vector.

2.2 Preparation of CGL (ΔldhA) Strain

The pK19 gapA::4G vector was introduced to CGL (Δldh) by electroporation. The strain wherein the pK19 gapA::4G vector was introduced was cultured at 30° C. by streaking the strain on LBHIS culture medium including kanamycin 25 μg/ml. The colony was streaked on LB-sucrose culture medium and cultured at 30° C. Then, only the colonies wherein double crossing-over occurred were selected. The genome DNA was separated from the selected colonies, and introduction of the 4G genes was verified through PCR by using primer sets 0049-1 for (SEQ ID NO:24) and 0049-2 rev (SEQ ID NO:25). CGL (ΔAldh 4G) strain was obtained as a result.

Example 3. Preparation of Strain Wherein adhE2 is Introduced 3.1 Preparation of pK19 gapA::adhE2 Vector To insert the adhE2 gene to the chromosome, the pK19 gapA::adhE2 vector for insertion of adhE2 gene was prepared on the basis of pK19 mobsacB. The pK19 gapA::adhE2 was prepared by synthesizing whole adhE2 gene having a nucleotide sequence of SEQ ID NO:26 and the cloning the adhE2 gene into the SmaI restriction enzyme site of the pK19 mobsacB vector.

3.2 Preparation of CGL (ΔldhA 4G adhE2) Strain

The pK19 gapA::adhE2 vector was introduced to CGL (Δldh 4G) by electroporation. The strain wherein the pK19 gapA::adhE2 vector was introduced was cultured at 30° C. by streaking the strain on LBHIS culture medium including kanamycin 25 μg/ml. The colony was streaked on LB-sucrose culture medium and cultured at 30° C. Then, only the colonies wherein double crossing over occurred were selected. The genome DNA was separated from the selected colonies, and introduction of the adhE2 gene was verified through PCR by using primer sets AdhE2_1_F for (SEQ ID NO:27) and AdhE2_2260_R (SEQ ID NO:28). CGL (ΔldhA 4G adhE2) strain capable of producing 1,4-BDO was obtained as a result.

Example 4. Screening of a Protein Related to Producing of 1,4-BDO

A wild type CGL and the mutant capable of producing 1,4-BDO, which was prepared above, were cultured in LB culture medium at 30° C. In an exponential phase of the wild type CGL and the mutant capable of producing 1,4-BDO (ΔldhA, cat1, sucD 4hbD, cat2, and adhE), 1,4-BDO of a concentration of 0, 25, 50, and 100 g/L was added to the culture medium at the time when the value of $OD_{600}$ was in the range from about 1.5 to about 2.5. Samples were taken at the time lapse of 0, 1, 3, and 5 hours, and expression of the total proteins was compared by 2D-gel electrophoresis (FIG. 3). Seven spots wherein electrophoresis expression intensity was increased in redundancy were selected (FIG. 4). Proteins of which electrophoresis expression level was increased in redundancy were identified as NCgl0827, NCgl2145, NCgl0630, and NCgl2826 by MALDI/MS.

Example 5. Preparation of a Strain, which is Capable of Producing 1,4-BDO, Over-Expressing a Screened Protein To verify whether or not a screened protein actually affects 1,4-BDO production, a microorganism wherein a screened protein is introduced was prepared. For this, a sequence encoding a screened protein was introduced into a vector, and the vector was in turn introduced into a CGL. The CGL was a strain which was transformed to be capable of producing 1,4-BDO. NCgl0630 gene (SEQ ID NO:2), NCgl2145 gene (SEQ ID NO:4), NCgl0827 gene (SEQ ID NO:5), and NCgl2826 gene (SEQ ID NO:6) were inserted into a MCS of pEKEx1 vector (a family of *Corynebacterium glutamicum/Escherichia coli* shuttle vectors for cloning, controlled gene expression and promoter probing. Gene, 102 (1991) 93-98) and then expressed by tac promoter. NCgl0630 gene was inserted by using the restriction enzymes EcoRI and SalI recognition sequences. NCgl2145, NCgl0827, and NCgl2826 genes were inserted by using the restriction enzymes BamHI and PstI recognition sites; restriction enzyme EcoRI (single) recognition site; and restriction enzymes EcoRI and BamHI recognition sites, respectively. A total of five strains were prepared by introducing expression vectors wherein each of the genes was introduced (pEK0630, pEK2145, pEK0827, and pEK2826)

and a pEKEx1 null vector (Ref) as a control group to a mutant strain CO24 (ΔldhA, cat1 sucD 4hbD cat2 adhE2) capable of producing 1,4-BDO.

Example 6. Comparison of 1,4-BDO Productivity of CGL Over-Expressing an Identified Gene 1,4-BDO productivity was compared after fermenting a total of five CGL mutants prepared above, including the control group. Firstly, to provide equal growth conditions, the strains were fermented under aerobic conditions. Fermentation was performed by changing the conditions into anaerobic conditions by reducing oxygen in culture medium after a predetermined time passed.

Colonies of the five mutants were injected respectively inoculated to LB culture medium 3 mL including kanamycin 25 μg/ml and cultured at 30° C. at a stirring rate of 220 rpm for 12 hours. The culture solutions were respectively inoculated to LB culture medium 50 mL including kanamycin 25 μg/ml and isopropyl β-D-1-thiogalactopyranoside (IPTG), which is a substance to induce expression of tac promoter, and cultured in 250 mL flasks at 30° C. at a stirring rate of 220 rpm for 24 hours. To change the culture conditions into anaerobic conditions, the culture solutions were respectively transported to 125 mL flasks and the flasks were sealed with film so that air might not be supplied. Then, the culture solutions were cultured at 30° C. at a stirring rate of 90 rpm for 72 hours. Cells of the strains were separated from the final culture solutions by centrifugation, and 1,4-BDO was quantified by analyzing supernatants by HPLC. 1,4-BDO productivity of the strains wherein NCgl0630 was expressed was 49% higher than that of the control group. 1,4-BDO productivity of the strains wherein NCgl2145 was expressed was 18% higher than that of the control group.

What is claimed is:

1. A *Corynebacterium glutamicum* microorganism capable of producing 1,4-butanediol (1,4-BDO),
wherein said *Corynebacterium glutamicum* microorganism is transformed with a nucleic acid comprising a nucleotide sequence encoding an amino acid sequence having at least 95% sequence identity with the amino acid sequence of SEQ ID NO: 3, and exhibits increased expression of the nucleic acid compared to a parent *Corynebacterium glutamicum* microorganism that is not transformed with the nucleic acid;
wherein the increased expression of the nucleic acid in said *Corynebacterium glutamicum* microorganism results in increased 1,4-BDO production compared to a parent *Corynebacterium glutamicum* microorganism capable of 1,4-BDO production that is not transformed with the nucleic acid; and
wherein said *Corynebacterium glutamicum* microorganism comprises genes encoding coenzyme A-dependent succinate semialdehyde dehydrogenase, 4-hydroxybutyrate dehydrogenase, 4-hydroxybutyryl CoA:acetyl-CoA transferase, and alcohol dehydrogenase.

2. The microorganism of claim 1, wherein the nucleotide sequence encoding an amino acid sequence having at least 95% sequence identity with the amino acid sequence of SEQ ID NO: 3 is the nucleotide sequence of SEQ ID NO: 4.

3. The microorganism of claim 1, wherein the microorganism further comprises a nucleic acid comprising a nucleotide sequence encoding citrate synthase.

4. A method of producing 1,4-BDO comprising:
   culturing the microorganism of claim 1, in a culture solution to produce 1,4-BDO; and
   obtaining the 1,4-BDO from the culture solution.

* * * * *